United States Patent [19]

Takahashi et al.

[11] 4,222,273

[45] Sep. 16, 1980

[54] DIGITAL TYPE ULTRASONIC HOLOGRAPHY APPARATUS

[75] Inventors: Fuminobu Takahashi, Kanagawa; Takahiro Kanamori, Tokyo; Kazumichi Suzuki, Kanagawa, all of Japan

[73] Assignee: Hitachi, Ltd., Japan

[21] Appl. No.: 917,600

[22] Filed: Jun. 21, 1978

[30] Foreign Application Priority Data

Jun. 22, 1977 [JP] Japan .................................. 52-73206
Sep. 28, 1977 [JP] Japan ............................... 52-115619

[51] Int. Cl.$^3$ ............................................. G01N 29/04
[52] U.S. Cl. ..................................................... 73/603
[58] Field of Search ................. 73/603, 604, 610, 611, 73/614, 615, 616; 340/5 H, 5 MP; 367/7, 8

[56] References Cited

U.S. PATENT DOCUMENTS

| | | | |
|---|---|---|---|
| 3,632,183 | 1/1972 | Halnes et al. | 340/5 H |
| 3,712,119 | 1/1973 | Cross et al. | 73/614 |
| 4,021,771 | 5/1977 | Collins et al. | 340/5 H |

OTHER PUBLICATIONS

Collins et al., "Acoustic Holographic Scanning Techniques for Imaging Flaws in Thick Metal Sections," Society of Photo-Optical Inst. Engineer Seminar, Feb. 1972, pp. 67–82.

*Primary Examiner*—Stephen A. Kreitman
*Attorney, Agent, or Firm*—Craig & Antonelli

[57] ABSTRACT

To provide an improved holographic operation, a digital type ultrasonic holography apparatus is provided utilizing a clock pulse generator having a predetermined periodicity, an ultrasonic pulse beam generator for directing an ultrasonic beam to an object for measurement in synchronism with said clock pulse, a reflected wave conversion unit for converting reflected ultrasonic pulse beams from said object for measurement into digital pulses, a time coincidence detector for detecting time coincidence between said clock pulse and said digital pulses contained in a predetermined gate period and producing as output a coincidence signal when they coincide with each other, a unit for moving an ultrasonic generating and receiving transducer included in said ultrasonic pulse beam generator to a desired position, and a display device for displaying the hologram of said object for measurement using said coincidence signal as a luminance signal and a position signal of said ultrasonic generating and receiving transducer as a deflection signal of said luminance signal. Using this holography apparatus a hologram of said object for measurement is displayed in a fringe pattern and the position and shape of said object for measurement are measured from those of the fringe pattern.

12 Claims, 31 Drawing Figures

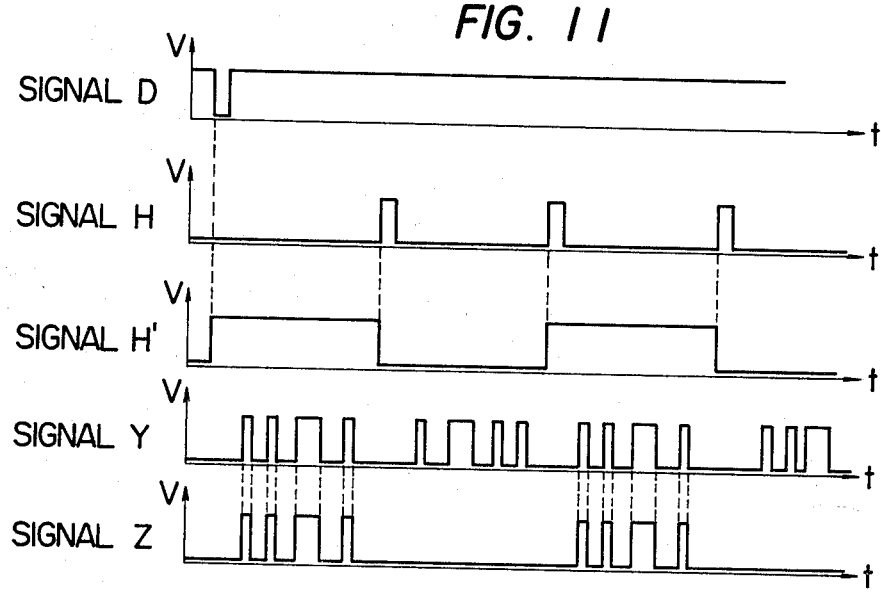
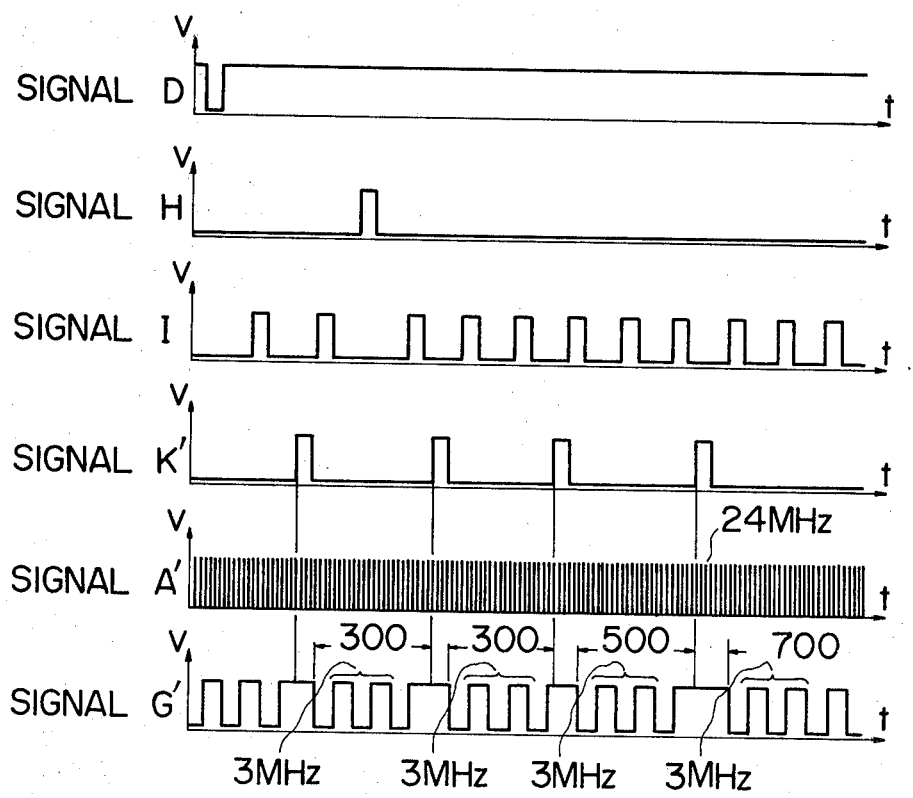

DIGITAL TYPE ULTRASONIC HOLOGRAPHY APPARATUS

BACKGROUND OF THE INVENTION

This invention relates to a holography apparatus for evaluating the size, shape and position of cracks present in the structure such as in the piping arrangement of an atomic reactor, for example, by the use of digital ultrasonic hologram.

The conventional ultrasonic holography apparatus obtains the information on cracks in an object by irradiating an ultrasonic pulse (transmission wave) of a sine wave mode from a transducer, receiving a reflected wave or transmission wave from the object (hereinafter referred to simply as "object modified wave"), causing the object modified wave to interfere with a reference wave having a predetermined phase difference from the transmission wave to obtain an interference wave, and luminance-modifying the amplitude of the interference wave so obtained to form an ultrasonic hologram of the object.

The apparatus of the above-described type is characterized in that it uses electric signals for the transmission wave and the reference wave so as to control the phase difference between them by an electric circuit and that the amplitude of the interference wave can be obtained by multiplication of the electric signals.

However, the conventional apparatus involves the following drawbacks. For one thing, since the transmission wave is caused to interfere with the reference wave, from several to dozens of seconds of pulse width of the received wave is required whereby the reflected waves from plural objects can not easily be discriminated with respect to time if the plural objects are present adjacent to each other. For another thing, since a ultrasonic pulse beam of a sine wave mode is transmitted from the transducer, the size of a receiver as well as a power amplifier become inevitably greater whereby maneuverability of the apparatus is lowered correspondingly. In addition, the gap of interference fringes of the resulting hologram is restricted depending on the ultrasonic frequency used.

SUMMARY OF THE INVENTION

It is an object of the present invention to provide a holography apparatus capable of changing the gap of interference fringes without any restriction on the frequency of the ultrasonic wave to be used.

It is another object of the present invention to provide a holography apparatus capable of easily discriminating timewise reflected waves from a plurality of adjacent cracks.

It is a further object of the present invention to provide a holography apparatus capable of easily controlling the mutual phase between the reference wave and the object modified wave.

It is a still further object of the present invention to provide a holography apparatus which consumes less power and is compact in size and light in weight.

In order to accomplish the abovementioned objects, the holography apparatus in accordance with the present invention comprises first means for generating a clock pulse having a periodicity 1/N Hz (where N is a positive integer), second means for transmitting an ultrasonic pulse beam to an object for measurement in synchronism with a pulse obtained by frequency-dividing the first clock pulse, third means for receiving the object modified pulse in the ultrasonic pulse beam and converting the object modified wave into a digital pulse, fourth means for detecting time coincidence between the first clock pulse and the digital pulses received within a predetermined gate period and generating a coincidence signal when they coincide with each other, and means for preparing a hologram of the object from the coincidence signal.

Although the hologram formed by the abovementioned apparatus can be used for evaluating the size, shape and position of cracks, it is not well suited for obtaining the reproduced image of the hologram as mentioned previously.

Accordingly, it is still another object of the present invention to provide a holography apparatus capable of forming a hologram which provides a clear reproduction image at the time of reproduction.

In order to accomplish the object mentioned above, the holography apparatus of the present invention further includes eighth means for holding the peak value of a detection signal of the object modified wave obtained from the abovementioned pulse conversion means for a predetermined period, ninth means for adding or subtracting respectively the peak value signals in response to coincidence or discordance between the coincidence signal and the peak value signal held by said first means during a predetermined gate period, tenth means for holding the output value of said second means at completion of said gate period for a predetermined period and means for forming the hologram of the object from the output signal of said third means.

BRIEF DESCRIPTION OF THE DRAWING

FIG. 3 shows an example of circuit of the twin clock pulse generator 13 of FIG. 2;

FIGS. 10 and 11 show time charts of the signals in the circuit of FIG. 9;

FIG. 16 shows a time chart of the signal in the circuit of FIG. 15;

DESCRIPTION OF THE PREFERRED EMBODIMENTS

The principle of the apparatus of the present invention will be explained with reference to the principle of the conventional apparatus using a sine wave. By way of example, the explanation is made in the case where the apparatus of the invention is used as a crack-detector.

Figure 1:
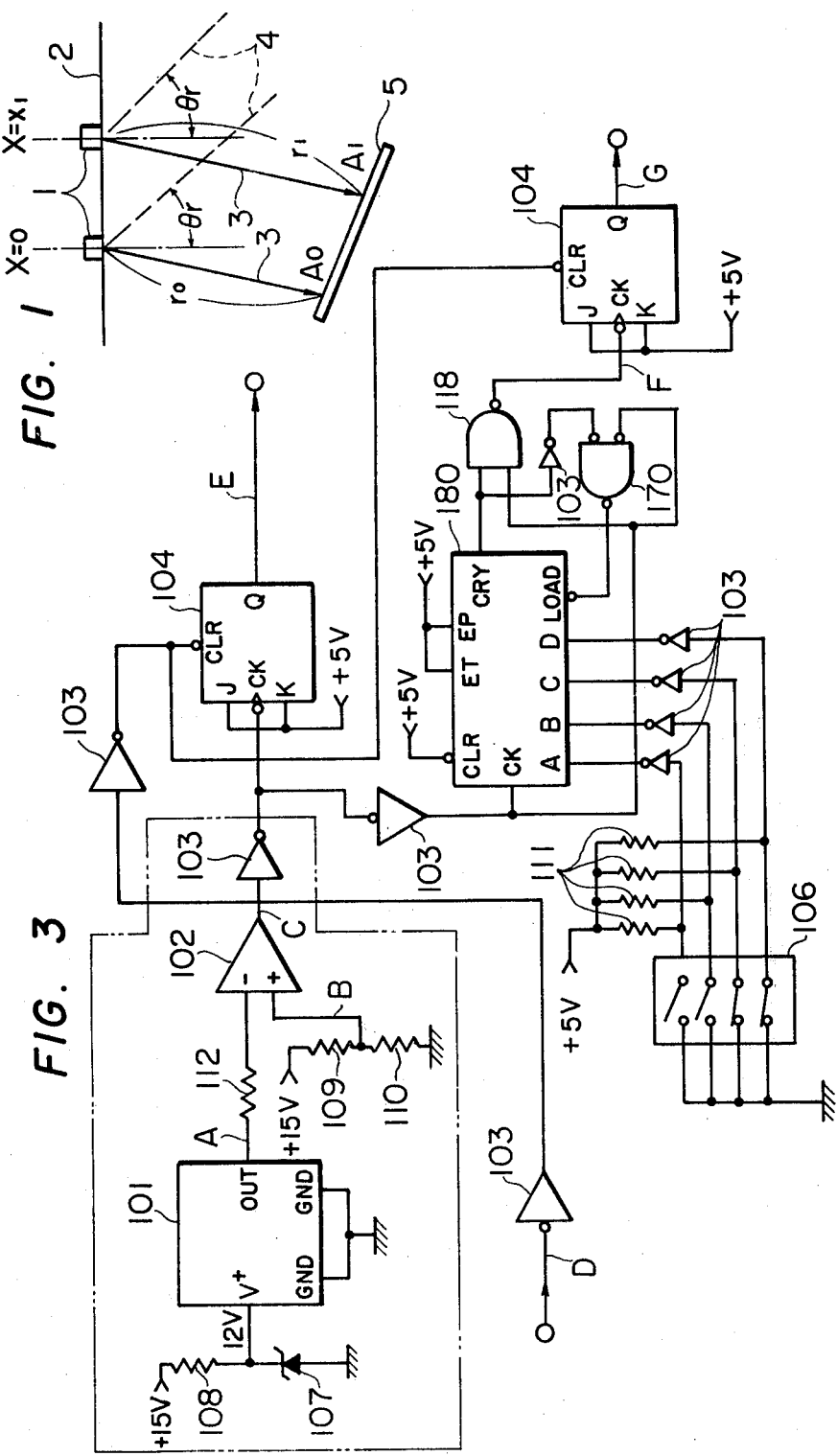
FIG. 1 shows the geometrical disposition of the transducer and the object in the ultrasonic holography apparatus.

It will be first assumed that reflected waves from an object 5 shown in FIG. 1 are observed by the use of a transducer having N MHz frequency. In FIG. 1, reference numeral 1 is the transducer which scans at a velocity Vs along a scanning line 2. When the transducer 1 is present at origins $X=0$ and $X=x_1$ of the scanning line 2, the ultrasonic beam 3 transmitted from the transducer 1 is incident at points $A_o$ and $A_1$ on the object 5, is reflected by the same and again incident to the transducer 1. In this case, the distance between the transducer 1 vs. the points $A_o$ and $A_1$ is $r_o$ and $r_1$, respectively, and the velocity of sound in the medium is va. The reference wave 4 is assumed to fall onto the transducer 1 at an angle $\theta r$.

In the conventional ultrasonic holography, the transmitted wave $\phi$ can be expressed as follows, assuming the transmission time of the ultrasonic pulse beam as the time origin;

$$\phi = I_o \omega t \quad (1)$$

where $I_o$ is intensity and $\omega$ is an angular frequency of the ultrasonic wave, that is, $\omega = 2\pi/N$ (1/sec).

Since there is a time lag from the transmission to the reception, the reflected wave or the transmitted wave from the object can be expressed as follows;

$$\phi d = I_d e^{i\omega(t - td)} \quad (2)$$

where $I_d$ is the intensity and td is the time lag.

The time lag td is determined by the propagation distance r of the ultrasonic wave from the transmission to the reception and the velocity of sound va in the medium through which it has propagated and expressed by the following equation;

$$td = r/va$$

Hence, the formula (2) can be re-formulated as follows;

$$\phi d = I_d e^{i(\omega t - kr)} \quad (2)'$$

where $k = 2\pi N/va$

The reference wave $\phi r$ incident to the transducer is expressed as follows in the case of FIG. 1;

$$\phi r = I_r e^{i(\omega t + kx \cdot \sin \theta r)} \quad (4)$$

As both reflected wave from the object and reference wave are simultaneously incident to the transducer 1, the transducer eventually receives the interference wave formed by the interference of the reflected wave $\phi d$ and the reference wave $\phi r$. The interference wave $\phi c$ can be expressed as follows;

$$\phi_c = \phi d \cdot \phi r^* + \phi d^* \cdot \phi r \quad (5)$$
$$= I_d \cdot I_r \cos k \cdot (r + x \sin \theta_r)$$

where the asterisk (*) represents conjugate complex numbers.

As shown in the formula (5), it can be appreciated that the interference wave does not oscillate time-wise but becomes a standing wave. The amplitude is determined by the propagation distance of the ultrasonic wave, the position of the transducer and the incident angle of the reference wave.

When the transducer is caused to scan, the condition required for the interference wave amplitude to score a positive value is as follows;

$$(2n - \tfrac{1}{2})\pi \leq k(r + x \sin \theta_r)(2n + \tfrac{1}{2})\pi \quad (6)$$

where n is an integer.

In other words, if the positive interference wave amplitude is used as a luminance signal, there are repeatedly present those positions which satisfy the condition of the formula (6) and can be expressed as interference fringes. This is the ultrasonic hologram of the object.

In the conventional holography apparatus, the object modified wave only is received by the transducer and a wave obtained by converting this object modified wave into an electric signal is caused to electrically interfere with an electric reference wave. The electric reference wave in this case is produced by deviating the phase of an electric signal of a sine wave mode oscillating the transducer by the use of a phase shifting circuit. Phase control shifts in comparison with the transducer position x as shown in the formula (4).

On the other hand, the principle of the first apparatus in the present invention corresponds to an ultrasonic holography when the incident angle $\theta r$ of the reference wave is made 0° in FIG. 1 (this is called Gavoa type holography). Namely, there is used a clock pulse having a frequency N MHz, a duty ratio of 50% and an output of 0-1 pattern as the reference wave and a ultrasonic pulse beam is generated from the transducer in synchronism with the rise of the clock pulse. Alternatively, the clock pulse is generated in synchronism with the generation of the ultrasonic pulse beam.

If the propagation distance of the ultrasonic wave is r, the object modified wave is received at r/va second(s) after the transmission. At the time of the reception, therefore, detection is made whether the output level of the clock pulse is 0 or 1. When the output level is 1, for example, the following formula is satisfied;

$$2n/2N \leq r/va \leq (2n+1)/2N \qquad (7)$$

where n is an integer. Since k=2 N/va, the formula (7) can be re-formulated as follows;

$$2n\pi \leq kr \leq (2n+1)\pi \qquad (7)'$$

The formula (7)' is the same conditional formula as when $\theta_r=0°$ in the formula (6). In other words, if time coincidence is measured between the received pulse (electric object-modified wave) and the clock pulse (electric reference wave) and the resulting coincidence signal is used as the luminance signal, it can be expressed as the interference fringe in the same way as in the conventional Gavoa type ultrasonic holography, thereby providing the ultrasonic hologram of the object.

Next, the explanation will be given on the principle of the second apparatus of the present invention.

This principle corresponds to the conventional ultrasonic holography when the reference wave is inclined.

For example, when a clock pulse of a frequency of N MHz, a duty ratio of 50 % and an output level of a 0-1 pattern is used and the position of the transducer is x, the transducer generates an ultrasonic wave beam at x·sin $\theta_r$/va second(s) after the rise time of the clock pulse. If the propagation distance of the ultrasonic wave is r, the object modified wave is received at r/va second(s) after generation of the beam. At this reception time, detection is made if the output level of the clock pulse is 0 or 1. If the output level is 1, for example, the following conditional formula is established;

$$(2n/2N - x\cdot\sin\theta_r/va) \leq r/va \leq (2n+1)/N - (x\cdot\sin\theta_r/va) \qquad (8)$$

where n is an integer.

Hence, the formula (8) can be re-written as follows;

$$2n\pi \leq k(r + x\cdot\sin\theta_r) \leq (2n+1)\pi \qquad (8)'$$

This formula (8)' is the same conditional formula as the formula (6).

In other words, by controlling the generation timing of the ultrasonic wave beam with respect to the clock pulse and using the coincidence signal between the received pulse and the clock pulse, it is possible to display the interference fringe in the same way as in the conventional ultrasonic holography in which the reference wave is inclined. This is the principle of the second apparatus of the present invention.

In the abovementioned second principle, the same effect can be obtained by controlling the generation timing of the clock pulse instead of retarding the generation timing of the ultrasonic wave beam from the rise of the clock pulse.

Namely, the clock pulse is generated at (CN−x·sin $\theta_r$)va second(s) after the generation of the ultrasonic wave beam when the transducer is at the position x. In this instance, C represents an optional integer. If the time coincidence is measured between the received pulse and the clock pulse in this manner, the formulas (7) and (7)' can be established, thereby enabling to obtain the ultrasonic hologram of the object. This is the principle of the third apparatus of the present invention.

Next, the explanation will be given on the principle of the fourth apparatus of the present invention.

First, a time t is measured from the generation timing of the ultrasonic pulse beam to the reception timing of the received pulse. A value x·sin $\theta_r$ depending on the position x of the transducer is added to the measured time t and multiplied by the frequency N. A luminance signal is generated when the fraction of this value is not greater than ½. The conditional formula in this case is as follows;

$$n \leq N(t + x\cdot\sin\theta_r/va) \leq n + \tfrac{1}{2} \qquad (9)$$

where n is an integer.

In the formula (9), since t=r/va and k=2πN/va, the formula (9) is expressed as follows;

$$2n\pi \leq k(r + x\cdot\sin\theta_r) \leq (2n+1)\pi \qquad (9)'$$

As can be seen, the formula (9)' is in conformity with the formula (8)'. In other words, it is possible to display the interference fringe in the same way as in the conventional holography in which the reference wave is inclined, and to obtain the ultrasonic hologram of the object by the use of the abovementioned luminance signal.

Next, the explanation will be given on the embodiments of the ultrasonic holography apparatus constructed on the basis of the abovementioned principles.

Figure 2:
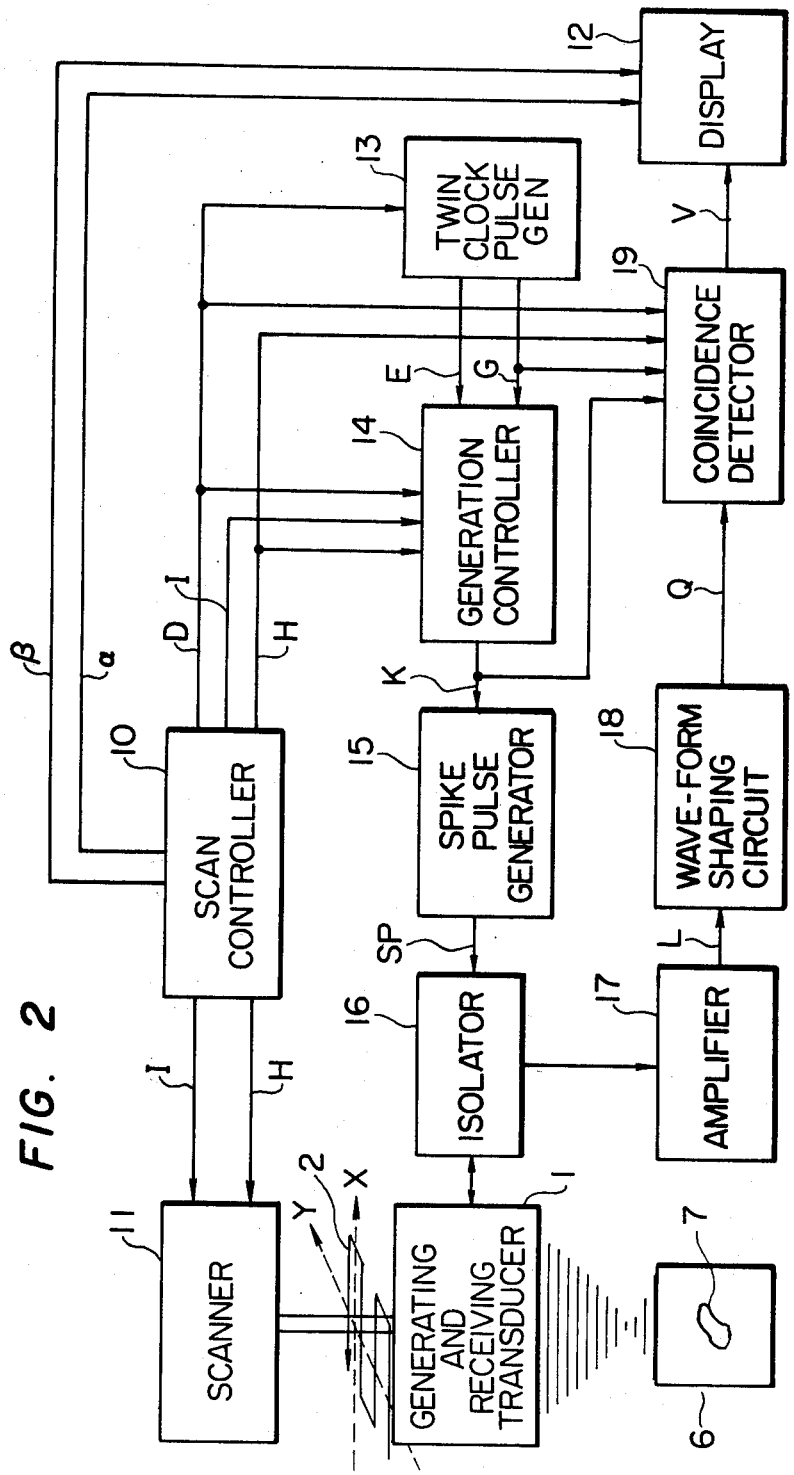
FIG. 2 shows the construction of the apparatus of FIG. 1.

FIG. 2 is a block diagram showing the overall construction of Example 1.

This Example illustrates an example where the present invention is adapted to a pulse echo system which performs the generation and reception of the ultrasonic wave by the use of a single transducer.

As depicted in FIG. 2, the transducer 1 is caused to scan along the scanning route 2 on the X - Y plane by means of the scanner 11. The scan controller 10 produces as output and X-drive pulse as a drive control for the scanner and both X- and Y-coordinate signals indicating the transducer positions, respectively. The scan controller 10 also supplies a reset signal to the twin clock pulse generator 13.

The twin clock pulse generator 13 generates as output a clock pulse of nN MHz and a clock pulse of N MHz obtained by frequency-dividing the former by 1/n. The generation controller 14 wired to the controller 10 and the generator 13 generates as output, in each periodicity of k seconds, a trigger pulse after the lapse of time which is by integer times longer than the period of nN MHz clock pulse from the rise time of N MHz pulse.

The spike pulse generator 15 generates a spike pulse in synchronism with the trigger pulse from the generation controller 15, and the isolator 16 supplies the high voltage spike pulse from the generator 15 to the transducer 1 and a reflected wave signal from both surfaces and cracks 7 of the object for crack detection received by the transducer to the amplifier 17.

The amplifier 17 amplifies the reflected wave signal from the transducer 1 and supplies it to the waveform shaping circuit 18.

The waveform shaping circuit 18 detects the amplification signal from the amplifier 17, changes a detection signal exceeding a predetermined voltage to a digitized pulse and outputs it as the received pulse.

The coincidence detector 19 extracts only the received pulse due to the reflected wave of the crack 7, which is generated as the output within a predetermined period of time after the generation of the trigger pulse by the generation controller 14, out of a plurality of received pulses from the waveform shaping circuit 18. Furthermore, the detector 19 produces as its output a coincidence signal obtained by holding the output level of an N Hz clock pulse at the rise t time of the received pulse till the subsequent detection time, to the display 12.

The display 12 uses X- and Y-coordinate signals from the scan controller 10 as deflection signals and the coincidence signal as the luminance signal and displays the hologram of the crack 7. The explanation will now be given specifically on the circuit construction as well as on the principle of action about the instruments encompassed by thick frames in FIG. 2. Those instruments which are not encompassed are the same as those used in the aforementioned conventional holography apparatus.

Figure 4:
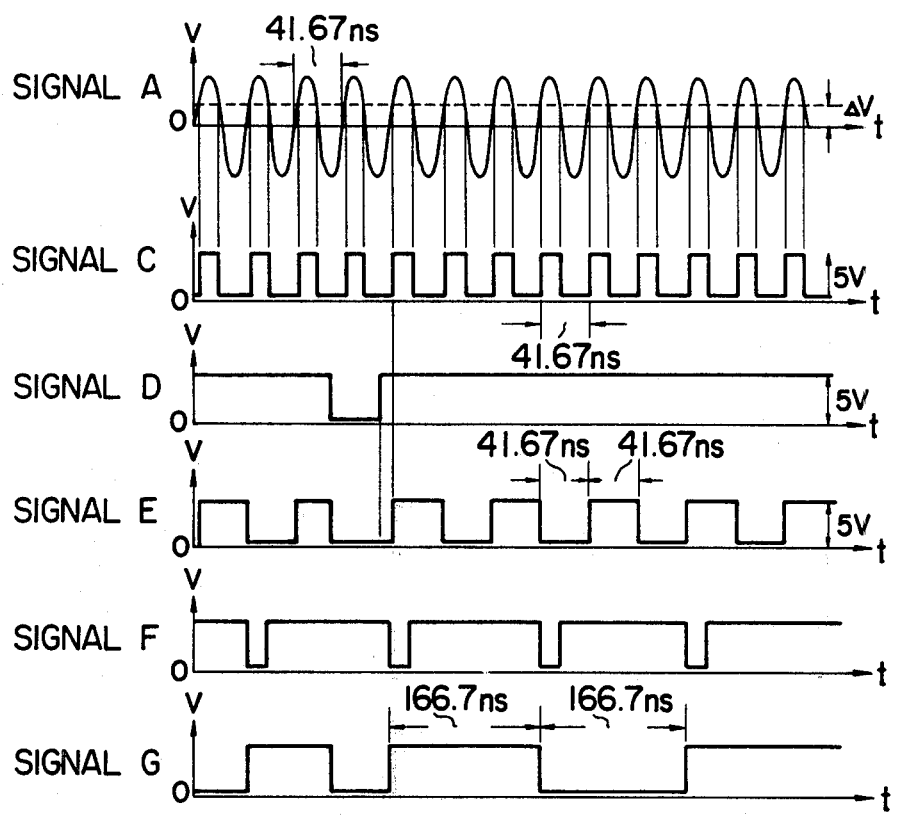
FIG. 4 shows a time chart of the signals in the circuit of FIG. 3.

FIG. 3 shows an example of the circuit of the twin clock pulse generator 13 wherein an element 101 is a 24 MHz crystal oscillator, an element 102 is a comparator, an element 103 is an invertor, an element 104 is a J - K flip-flop, an element 180 is a synchronous 4-bit counter, an element 118 is a NAND gate, an element 170 is an OR gate, an element 106 is a switch, an element 107 is a 12 V zenor diode, and elements 108 through 112 are resistors. FIG. 4 illustrates the time chart of the signals represented by A, B, C, D, E, F and G in FIGS. 2 and 3.

Symbol A in FIG. 4 represents the output signal of the crystal oscillator 101 which is 24 MHz, sine mode. The voltage level ΔV indicated by the dotted line is a threshold level of the comparator 102. Symbol C represents the output signal of the comparator 102 and becomes +5 V only when the signal A exceeds the level ΔV. Symbol D represents a reset signal produced as output from the scan controller 10. When the reset signal D drops down from 5 V to 0 V, the count number of the J - K flip-flop 104 is cleared. The signal E is an output signal of the J - K flip-flop which halves the frequency of the signal C; hence, there is produced a clock pulse of a duty ratio of 50% and a frequency of 12 MHz.

The signal F consists of a CARRY signal of the synchronous counter 180 and a NAND signal of the 24 MHz clock pulse C. Under the switching condition of the switch 106 shown in FIG. 3, a negative logic pulse indicated by the signal F is produced whenever the pulse number of the signal C is four.

A clock pulse having a duty ratio of 50% and a frequency of 12/N MHz (N=4 in FIG. 3) represented by a signal G is generated as output by halving the frequency of the signal F through the J - K flip-flop 104.

Figure 5:
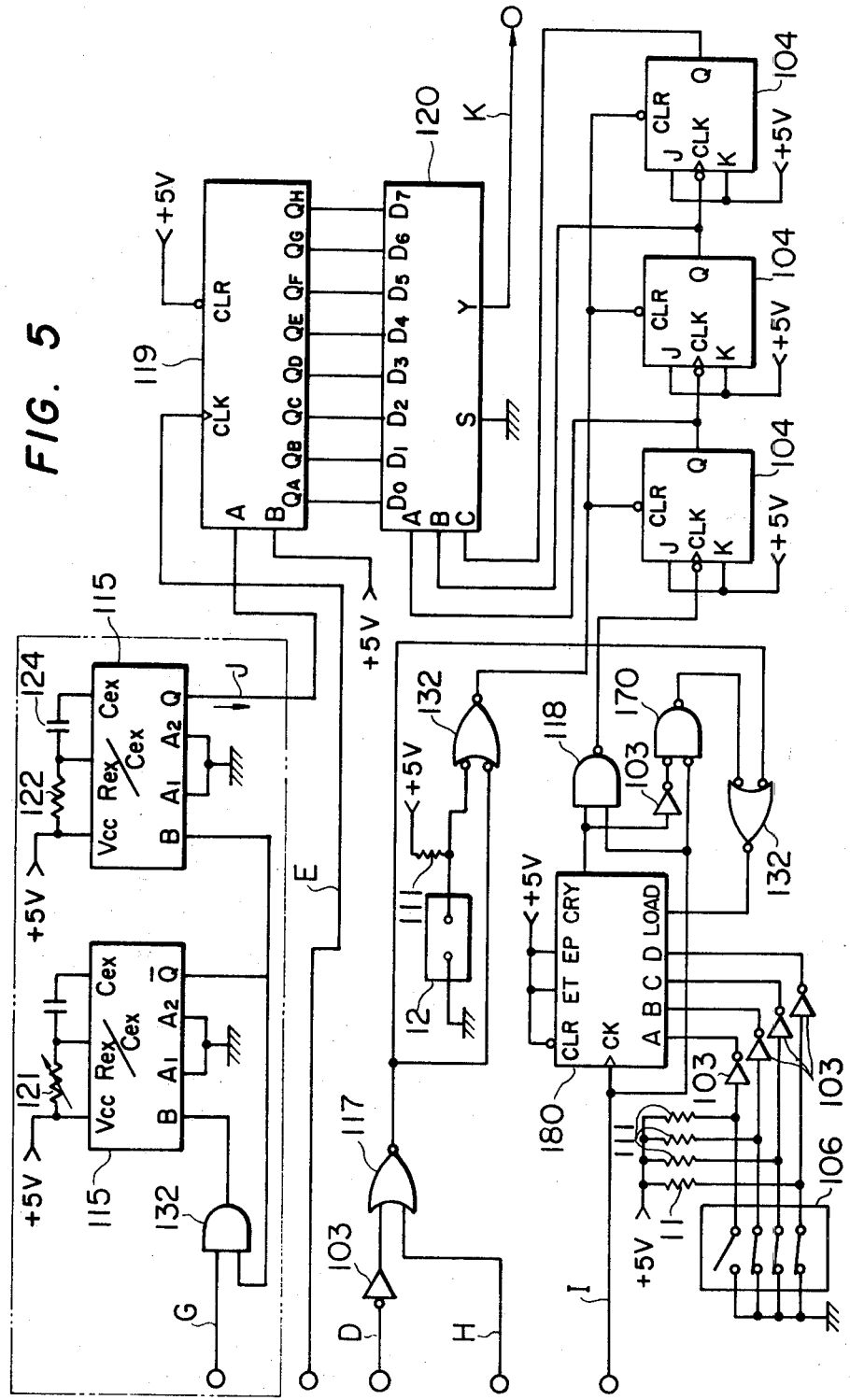
FIG. 5 shows an example of circuit of the generation controller 14 of FIG. 2.

FIG. 5 illustrates an example of the circuit of the generation controller 14 shown in FIG. 2, wherein an element 115 is a mono-stable multivibrator, an element 116 is an invertor, an element 117 is a NOR gate, an element 118 is a NAND gate, an element 119 is an 8-bit parallel-out shift register, an element 1120 is a data selector and, an element 132 is an AND gate. An element 121 is a variable resitor, elements 123 and 124 are capacitors and an element 112 is an ON-OFF switch.

Figure 6:
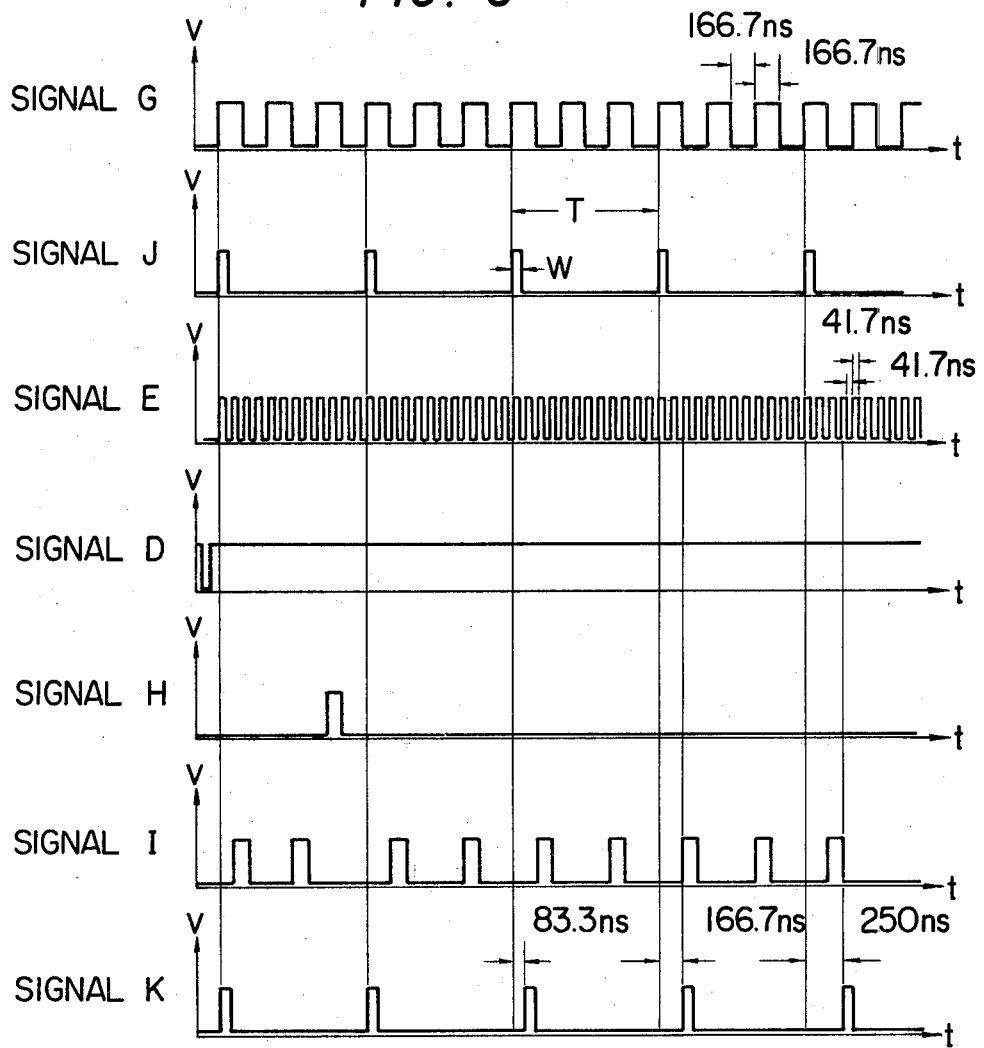
FIG. 6 shows a time chart of the signal in the circuit of FIG. 5.

FIG. 6 shows the time chart of the signals represented by G, E, D, H, I, J and K in FIG. 5.

In FIG. 6, the signals G and E are N MHz clock pulse and nN MHz clock pulse, respectively (n=4, N=3 in FIGS. 5 and 6) and both are output signals from the twin clock pulse generator 13 shown in FIG. 2. The signals D, H and I are output signals from the scan controller 10 (of FIG. 2) and represent respectively the reset pulse, Y-drive pulse and X-drive pulse.

The signal J represents a repeating periodicity pulse whose rise is in synchronism with that of the N MHz clock pulse (signal G). The repeating periodicity T is controlled by the resistance of the variable resistor 121 shown in FIG. 5. The pulse width W scores a value determined by the resistor 122 and the capacitor 124.

The signal K represents the trigger pulse when the ON-OFF switch 112 and the switch 106 are under the condition shown in FIG. 5. Namely, there is produced a trigger pulse (signal K) obtained by shifting the repeating periodicity pulse (signal J) by one 12 MHz clock pulse whenever the number of the X-drive pulse (signal I) increases by two after the output of either the reset pulse (signal D) or the Y-drive pulse (signal H). However, the time lag of the trigger pulse from the repeating periodicity pulse (signal D) is a time corresponding to maximum seven 12 MHz clock pulses. When a shift is made in the quantity corresponding to the seven 12 MHz click pulses, the trigger pulse again coincides with the repeating periodicity pulse, thereafter repeating sequentially the abovementioned shift. If the switch 112 is OFF, however, there is produced as output the trigger pulse in synchronism with the repeating periodicity pulse.

Figure 7:
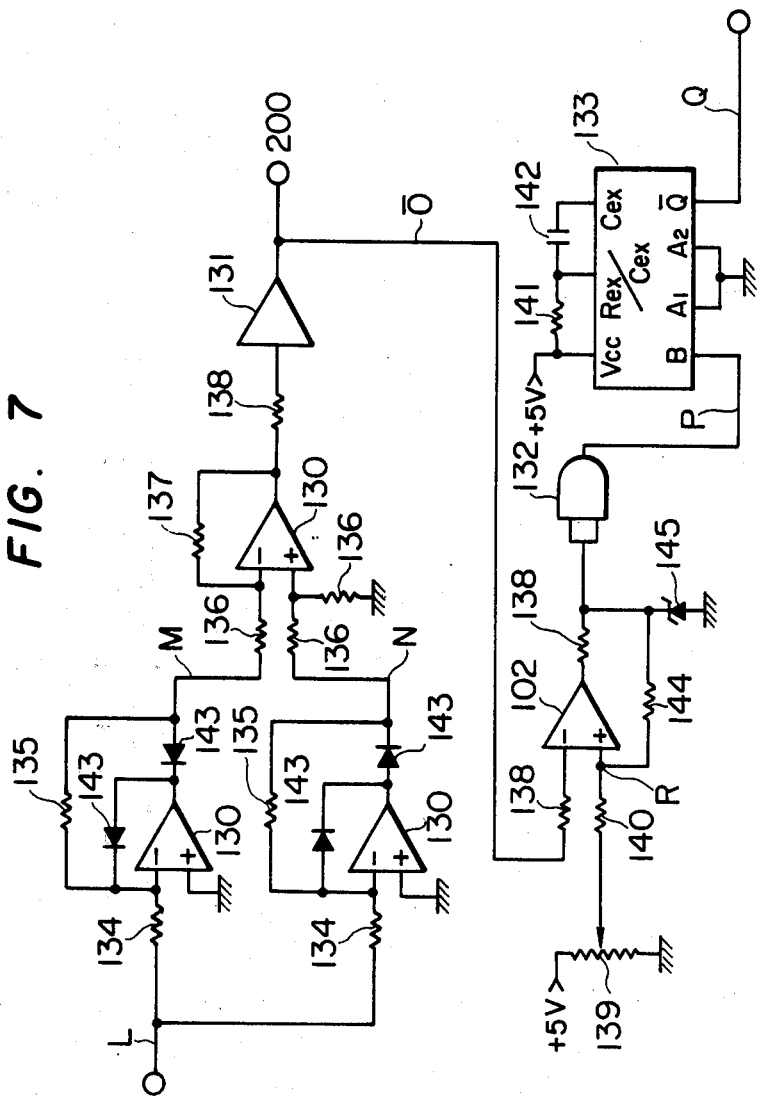
FIG. 7 shows an example of circuit of the waveform shaping circuit 18 of FIG. 2.
Figure 8:
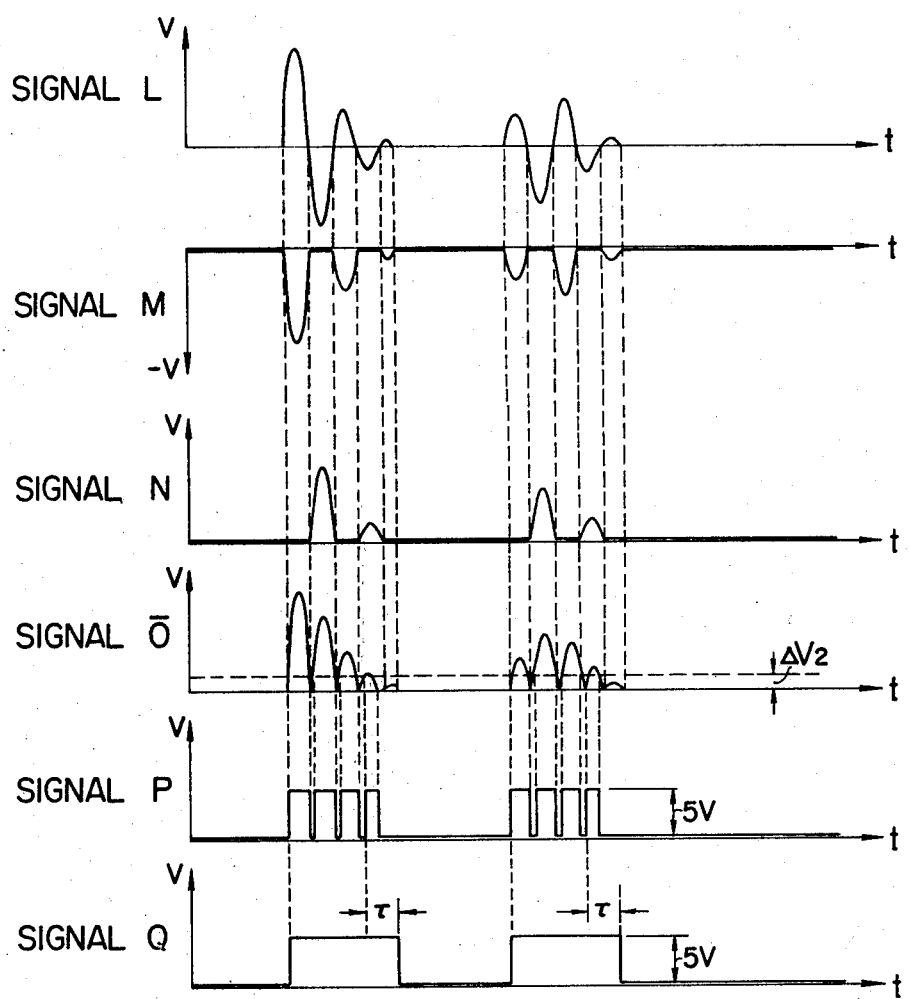
FIG. 8 shows a time chart of the signals in the circuit of FIG. 7.

FIG. 7 shows an example of the circuit of the waveform shaping circuit 18 shown in FIG. 2, in which an element 130 is an operation amplifier, an element 131 is a buffer amplifier, an element 132 is an AND gate, an element 133 is a re-triggerable multi-vibrator, elements 135 through 141 are resistors with the exception of an element 139 which is a variable resistor, an element 142 is a capacitor, an element 143 is a diode and an element 145 is a zener diode. Numeral 200 represents an output terminal of the detection signal. FIG. 8 shows the time charts of signals represented by L, M, N, $\overline{O}$, P and Q in FIG. 7.

The signal L of FIG. 8 is the amplitude signal from the amplifier 17 (FIG. 2) and the signal M is a signal obtained by amplifying only the positive portion of the signal L by the operation amplifier 130 and reversing its polarity. The signal N is a signal obtained likewise by amplifying only the negative portion of the signal L by the operation amplifier 130 and reversing its polarity.

The signal $\overline{O}$ is a differential amplification signal between the signals M and N. The voltage $\Delta V_2$ level indicated by the dotted line is a threshold level R of the comparator 102. The signal P is an output of the comparator 102 and becomes +5 V only when the signal $\overline{O}$ exceeds the threshold level. The signal Q is an output signal of the waveform shaping circuit 18 and is obtained by applying the signal P as input to the re-triggerable multi-vibrator 133. As a result, it is possible to shape the waveform of the reflected wave pulse such as the signal L into the waveform of the received signal such as the signal Q.

Figure 9:
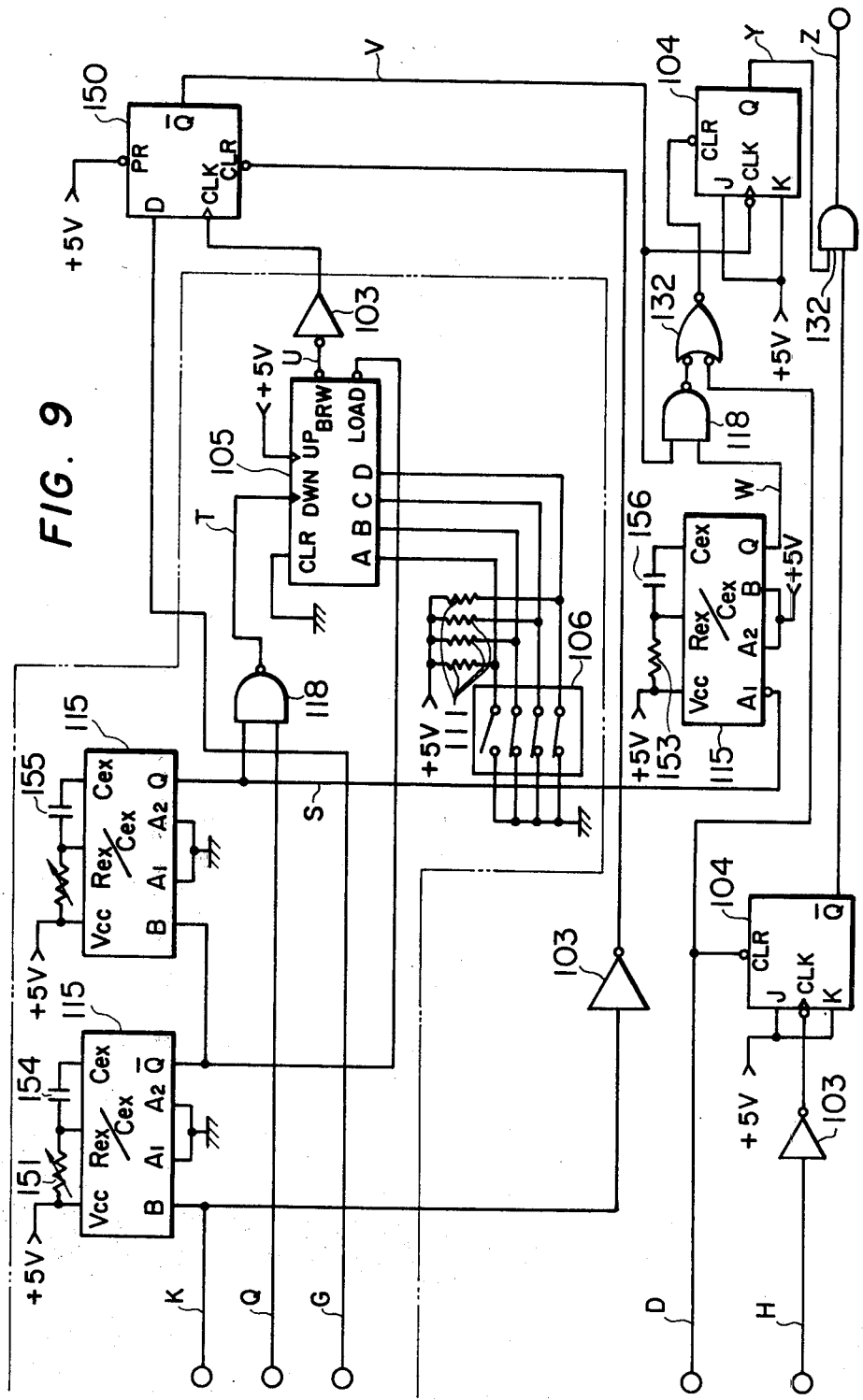
FIG. 9 shows an example of circuit of the coincidence detector 19 of FIG. 2.
Figure 10:
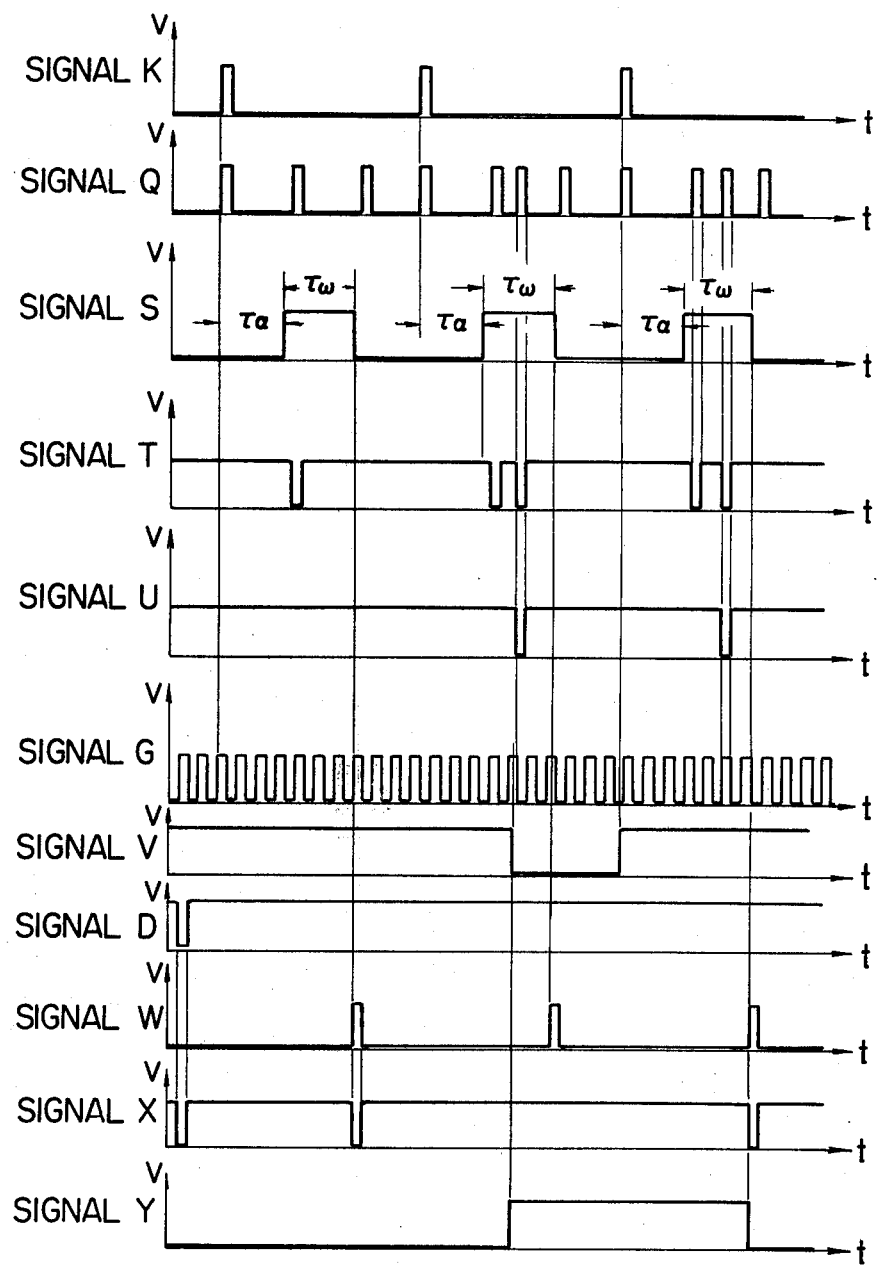

FIG. 9 shows an example of the circuit of the coincidence detector 19 shown in FIG. 2, wherein an element 105 is a 4-bit up-down counter, an element 150 is an edge trigger flip-flop, elements 151 and 152 are variable resistors, an element 153 is a resistor and elements 154 through 156 are capacitors. FIGS. 10 and 11 show the time chart of the signals represented respectively by K, Q, S, T, U, G, V, D, W, X, Y, Z, H and H' in FIG. 9.

The signal K is a trigger pulse generated as output from the generation controller 14 (FIG. 2). The signal Q is a received pulse from the waveform shaping circuit 18 (FIG. 2) and the signal G is an N MHz clock pulse from the twin clock pulse generator 13 (FIG. 2) (N=3, or, 3 MHz in this case). The signals D and H are respectively a reset pulse and a Y-drive pulse generated from the scan controller 10 (FIG. 2).

The signal S is a gate pulse and is produced by two mono-stable multi-vibrators 115. The gate pulse (signal S) rises at $\tau d$ seconds after the rise of the trigger pulse (signal K) and its width is $\tau w$ seconds. $\tau d$ is determined by the time constant of the variable resistor 151 and that of the capacitor 154 while $\tau w$ is determined by the time constant of the variable resistor 152 and that of the capacitor 155.

The signal T is a NAND signal of the signals Q and S. That is to say, the gate pulse (signal S) is a signal for extracting the received pulse which is received within a predetermined period of time after generation of the ultrasonic pulse beam.

The signal T is applied as input to the 4-bit up-down counter 105 and produces as output only the pulse of the Jth number among the received pulses within the gate pulse generation time as a BORROW (signal U). (J=2 in the switching state of the switch 106 shown in FIG. 9.)

The edge trigger flip-flop 150 reads the output level of the N MHz clock pulse at the time of fall of the signal U (i.e., signal G) and produces the signal V (coincidence pulse) that holds the reversion level of the readout level till the rise time of the subsequent trigger pulse. The signal W is a pulse in synchronism with the fall of the gate pulse (signal S), which is produced by the mono-stable multi-vibrator 115. Its pulse width is determined by the resistor 153 and the capacitor 156. The signal X is an AND signal between the signal D (reset pulse) and the NAND signal between the signals W and V. The signal Y is produced from the signal V by converting the signal X to a clear signal of the j - K flop-flop 104. J - K flip-flop 104 which counts the Y-drive pulse (signal H) after the output of the reset pulse. The signal Z is obtained by taking AND between the signal H' and the signal Y and is generated as an output coincidence signal.

In other words, when the signal H' is at the level "1", it corresponds to the case where the transducer is caused to scan in the forward direction of the X-axis, thereby generating as output only the coincidence signal at the time of scanning in the forward direction. In this manner, it is possible to minimize the deviation of the image on the display 12 arising from the mechanical idling of the scanner 11.

Next, the explanation will be given about the action of Example 1 shown in FIG. 2.

The scan controller 10 generates as output the X- and Y-drive pulses for actuating the X- and Y-drive motors of the scanner 11 and causes the transducer fitted to the scanner 11 to scan along the scanning route 2. The scan controller 11 generates as output the reset pulse for clearing in advance the counter of each circuit before the start of scanning and X- and Y-coordinate signals that respectively represent the position of the transducer on the X- and Y-axes in terms of voltage.

The twin clock pulse generator 13 generates as output the nN MHz clock pulse and the N MHz clock pulse obtained by dividing the frequency of the former by n (duty ratio=50%). The generation controller 14 generates as output a trigger pulse in synchronism with the rise of the nN MHz clock pulse of the mth number (m=0-7 in this example) counted from the rise of the N MHz clock pulse with a predetermined periodicity in accordance with the count number 1 of the X-drive pulse after generation of either the reset pulse or the Y-drive pulse.

The spike pulse generator 15 generates as its output a high voltage spike pulse in synchronism with the trigger pulse. The spike pulse is impressed to the transducer 1 through the isolator 16 and the ultrasonic wave is transmitted from the transducer. The ultrasonic wave so transmitted is incident to the sample 6, reflected by its front and back surfaces or by the crack 7 and is again incident to the transducer 1. The reflected wave received by the transducer 1 is converted into an electric signal and applied as input to the amplifier 17 through the isolator 16.

The amplifier 17 amplifies the input reflected wave signal and generates it as the output amplification signal to the waveform shaping circuit 18. The waveform shaping circuit 18 detects the amplification signal, forms a detection signal and generates as output a received pulse of a digitized pulse for the detection signals which exceed a predetermined threshold level. The coincidence detector 19 extracts only the received pulse among those applied as input within a predetermined period of time after the generation of the trigger pulse and also generates a coincidence signal holding the output level of the N MHz clock pulse at the time of rise of the extracted received pulse. However, when there is no received pulse within the predetermined period of time after generation of the trigger pulse, the output level of the coincidence signal becomes zero (0). Also, when the transducer 1 is caused to scan on the X-axis in the reverse direction, the output level of the coincidence signal becomes 0. (Setting may be made so that the output level becomes 0 when the transducer is caused to scan in the forward direction.) Scanning on the X-axis in the reverse direction can be found when the count number of the Y-drive pulse after generation of the reset pulse is an odd number. The hologram is displayed on the display 12 by the use of the abovementioned coincidence signal as the luminance signal and X- and Y-coordinate signals as the deflection signals.

Figure 12:
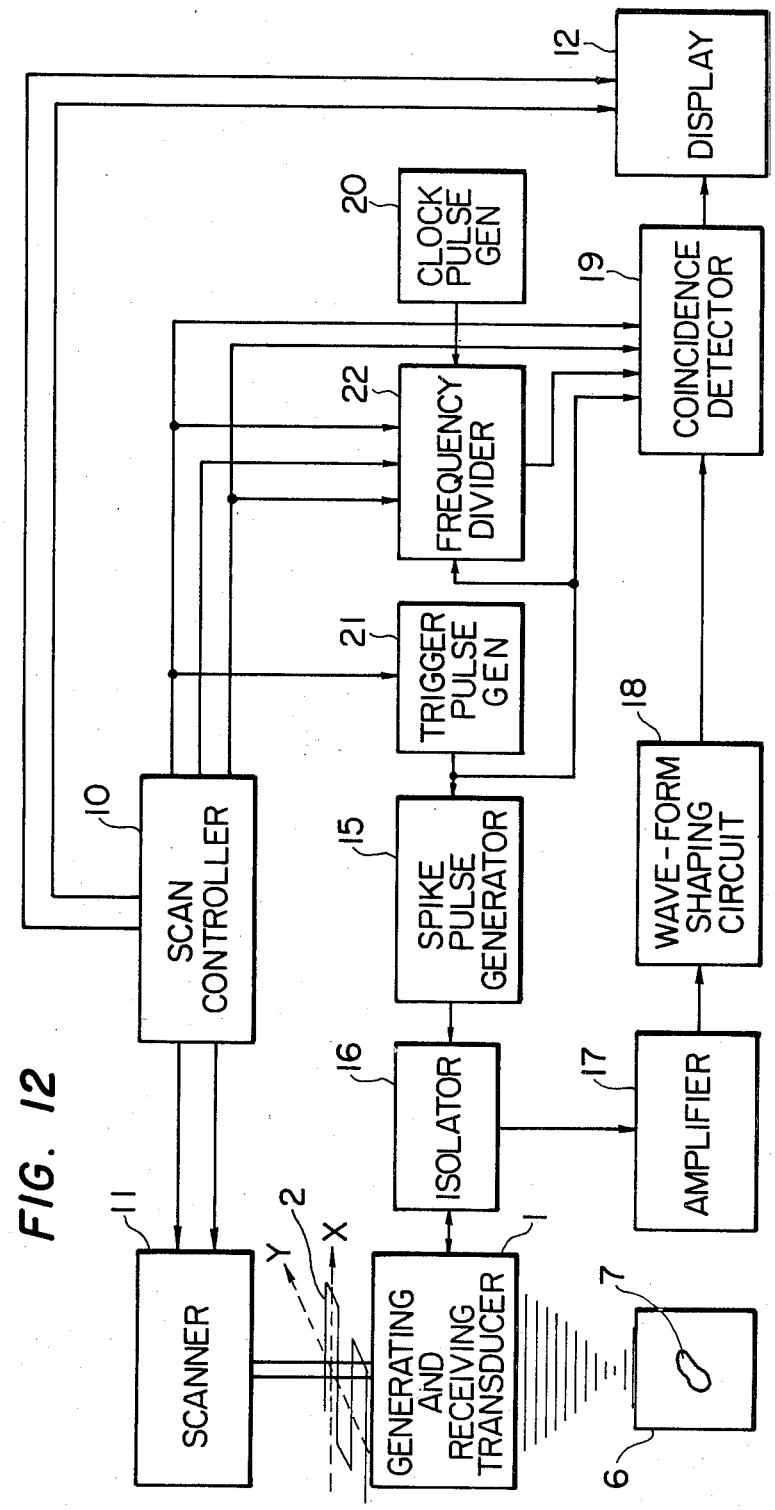
FIG. 12 shows the construction of the apparatus of Example 2 of the present invention.

FIG. 12 is a block diagram showing the overall construction of the apparatus of Example 2 of the present invention. In FIG. 12, constituent elements different from those of Example 1 (shown in FIG. 2) are indicated by thick frames.

In Example 1, the generation timing of the ultrasonic pulse beam is retarded from the rise time of the N MHz clock pulse. In this Example 2, on the other hand, the generation of N MHz clock pulse is retarded from the generation timing of the ultrasonic wave beam. This Example 2 is further characterized in that the generation of the ultrasonic pulse is out of synchronism with the clock pulse from the clock pulse generator 20.

Since the signal processing steps ranging from the generation of the ultrasonic pulse beam, shaping of the reflected wave signal up to the display of the hologram by means of the coincidence signal are exactly the same as in Example 1, the explanation is hereby deleted. Hence, the following explanation deals with the circuit construction and the action of the pulse generators 20, 21 and the frequency divider 22.

The clock pulse generator 20 generates a 2nN MHz clock pulse. It will be assumed that n=4 and N=3, for example. The circuit construction in this case is the same as the portion encircled by the dotted line in FIG. 3, and generates as output a 24 MHz clock pulse.

The trigger pulse generator 21 generates a trigger pulse irrespective of the output of the clock pulse generator 20.

Figure 13:
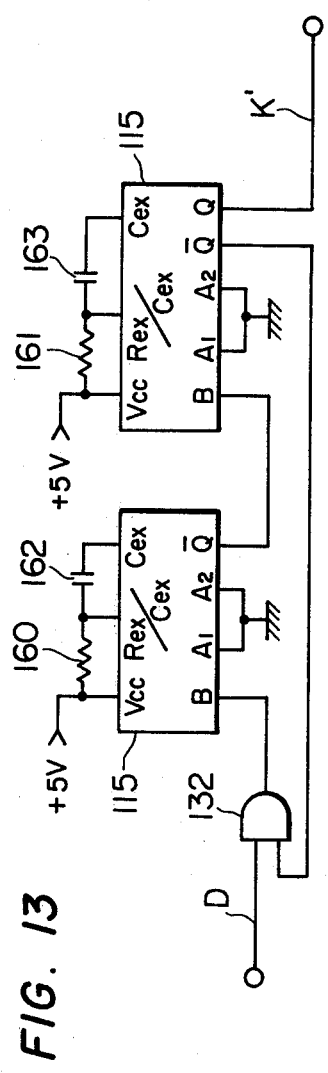
FIG. 13 shows an example of circuit of the trigger pulse generator 21 of FIG. 12.
Figure 14:
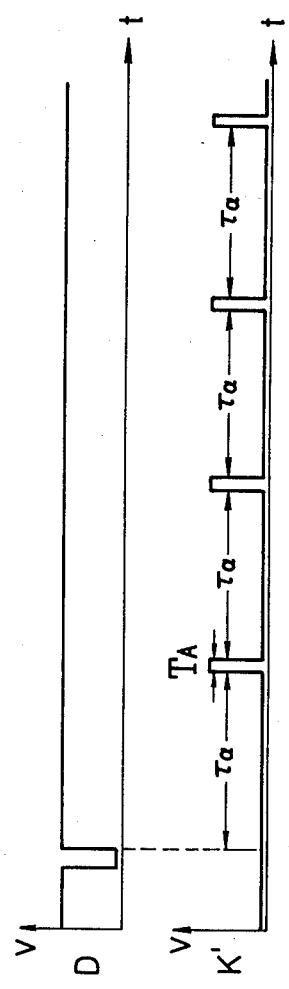
FIG. 14 shows a time chart of the signals in the circuit of FIG. 13.

FIG. 13 shows an example of the circuit construction of the trigger pulse generator 21. In FIG. 13, elements 160 and 161 are resistors and elements 162 and 162 are capacitors. FIG. 14 shows the time chart of the signals represented respectively by the symbols D and A'.

The signal D is a reset pulse generated as output from the scan controller 10 (FIG. 12). The signal K' is an output signal of the trigger pulse generator 21. The trigger pulse is generated at $\tau a$ seconds after the rise of the reset pulse (Signal D) with a pulse width of $T_A$ seconds. This pulse is sequentially generated with a time interval of $\tau a$ seconds. $T_A$ is determined by the time constant of the resistor 161 and that of the capacitor 163, while $\tau a$ is determined by the time constant of the resistor 160 and that of the capacitor 162.

Figure 15:
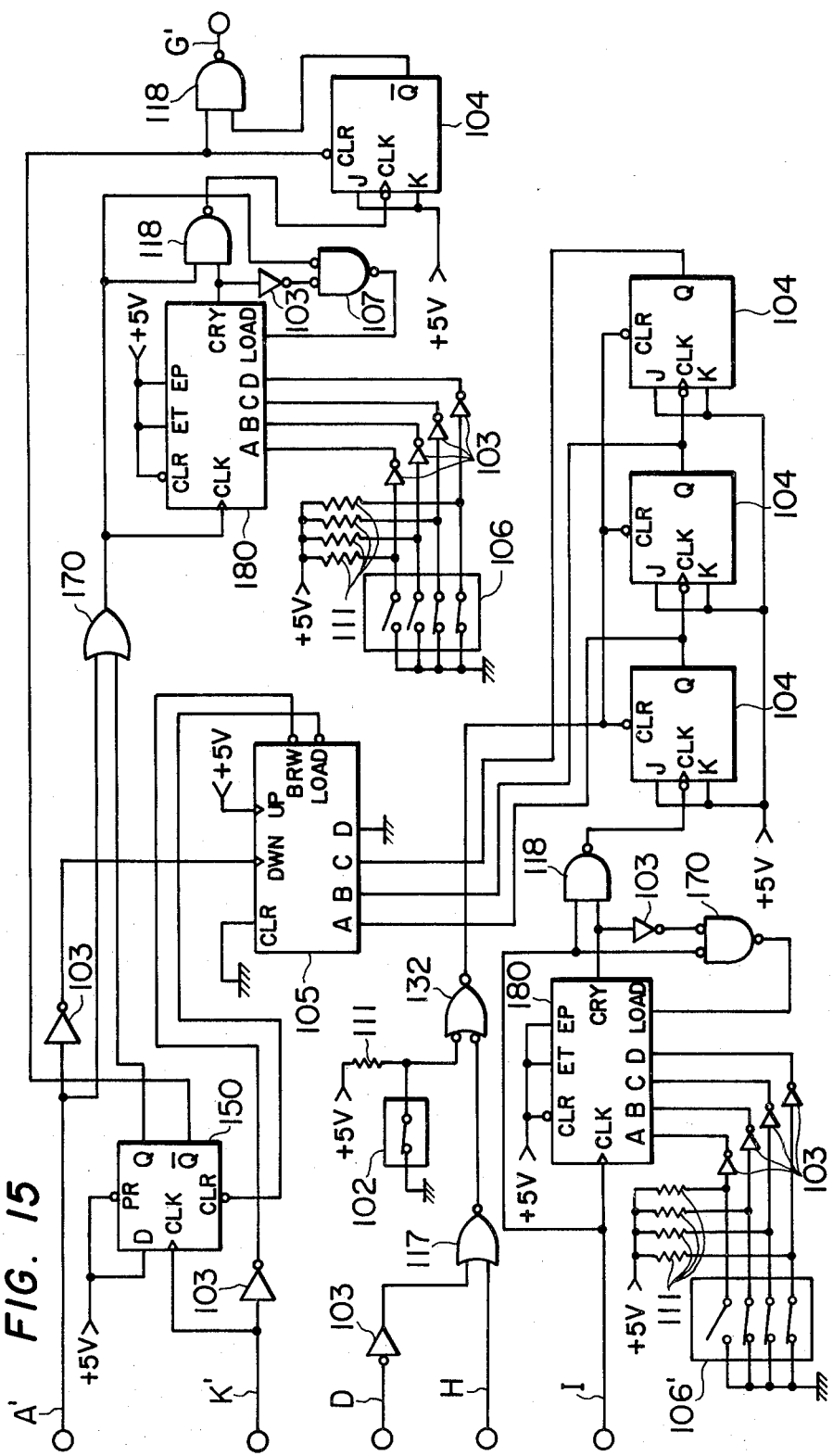
FIG. 15 shows an example of circuit of the frequency divider 22 of FIG. 12.

FIG. 15 shows an example of the circuit construction of the frequency divider 22 shown in FIG. 12.

In FIG. 15, elements 106, 106' are switches. The signal A' is a 24 MHz clock pulse from the clock pulse generator 20 and the signal K' is a trigger pulse from the trigger pulse generator 21. The signals D, H, I are respectively a reset pulse, a Y-drive pulse and an X-drive pulse, all being the signals from the scan controller 10 (FIG. 12). The signal G' is a 3 MHz clock pulse which is an output signal of the frequency divider 22.

FIG. 16 shows the time chart of these signals. Numeral 300 in the drawing represents a period corresponding to three K' pulses, and 500 and 700 represent respectively periods corresponding to five and seven K' pulses. The explanation will be given about the output level of the signal G'. The output level of the signal G' is in the state "1" at the rise of the signal K' (trigger pulse). The output level of this signal G' becomes "0" after (4+j) pieces of 24 MHz clock pulses (=A' pulses) are generated from its rise time. Thereafter, the output level of the signal G' changes by every four A' pulses so that the frequency becomes 3 MHz. In this instance, j is determined by the number of occurrence i of the X-drive pulse (signal I) after generation of the reset pulse (signal D') or the Y-drive pulse (signal H). When the switch 106 is in the switching state shown in FIG. 15, j scores a maximum integer value which does not exceed a value obtained by dividing i by 2. However, since i is counted as a digit of the octal notation and varies sequentially from 0 to 7, the value of j changes from 0 to 3, correspondingly.

In the abovementioned manner, the generation timing of the 3 MHz clock pulse (signal G') is controlled with respect to the trigger pulse (signal K') along with movement of the transducer 1 on the scanning route 2. It is also possible to generate the 3 MHz clock pulse (signal G') in synchronism with the trigger pulse (signal K') by turning off the ON-OFF switch 112 of FIG. 15.

Figure 17:
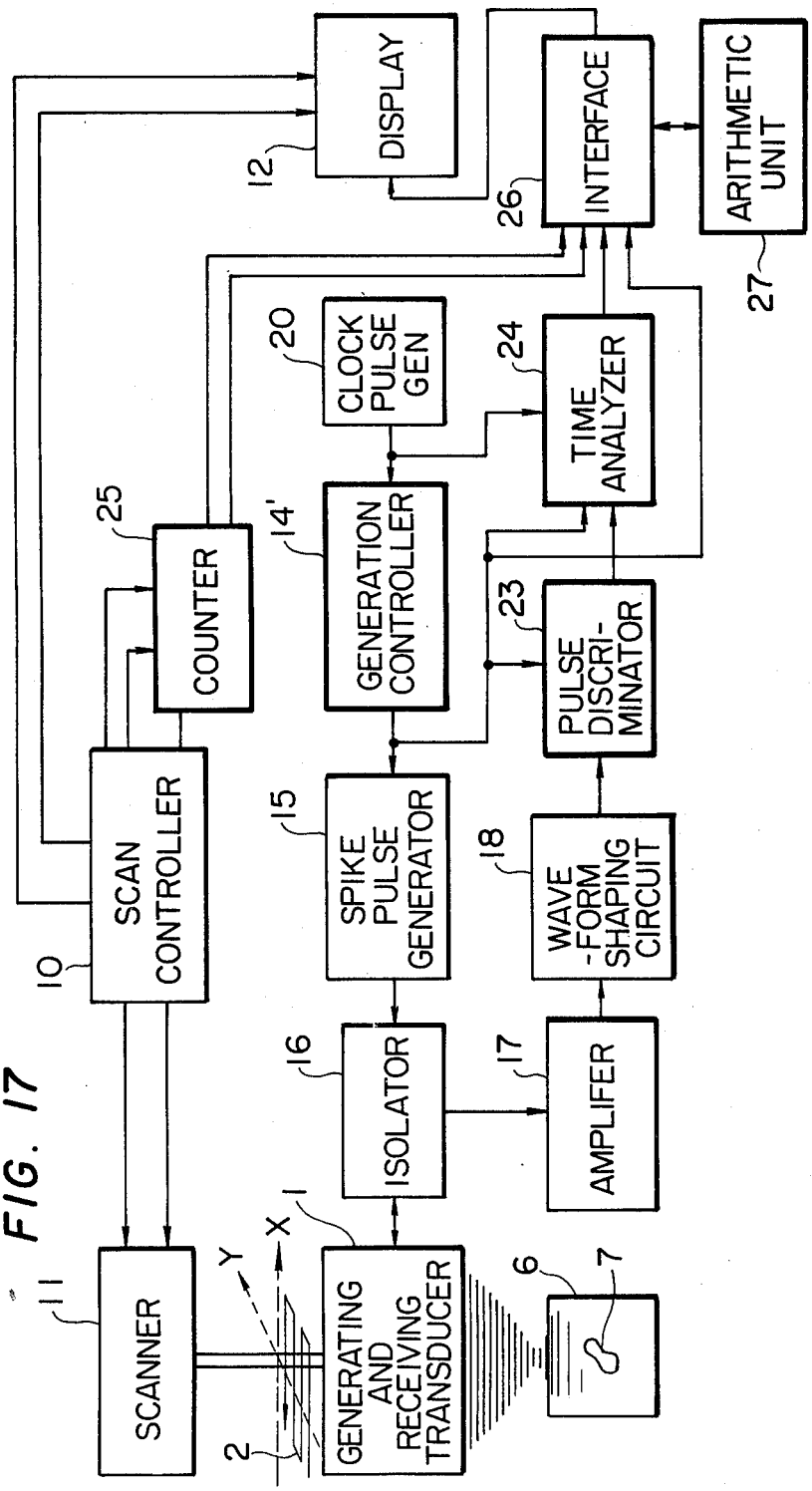
FIG. 17 shows the construction of the apparatus of Example 3 of the present invention.

FIG. 17 is a block diagram showing the overall construction of the apparatus in Example 3 of the present invention.

Unlike Examples 1 and 2 wherein the time coincidence is measured between the received pulse and the clock pulse, this Example is characterized in that it measures the time passed from the generating timing of the trigger pulse to the reception of the pulse, and a hologram signal (displayed as the luminance signal in FIG. 17) is operated and calculated from the time thus measured.

In the construction shown in FIG. 17, instruments other than those encircled by thick frames are the same as those of Examples 1 and 2 with the same reference numeral shown respectively in FIGS. 2 and 12. Hence, the following explanation is directed to the action of the instruments encircled by the thick frames.

The generation controller 14' generates a trigger pulse having a predetermined repeating periodicity and a predetermined pulse width in synchronisms with the rise of a 24 MHz clock pulse generated by the clock pulse generator 20. The spike pulse generator 15 generates a spike pulse in synchronism with the trigger pulse and a ultrasonic pulse beam is transmitted from the transducer 1. An example of the circuit construction of the generation controller 14' is shown by the portion encircled by the dotted lines in FIG. 5. However, a 3 MHz clock pulse is applied as input in FIG. 5 whereas this example obtains the trigger pulse (repeating periodicity pulse J being shown in FIG. 5) by applying a 24 MHz clock pulse as input.

The pulse discriminator 23 extracts only the received pulse which is formed by the reflected wave from the crack 7 among the received pulses from the waveform shaping circuit 18. An example of the circuit construction of this pulse discriminator 23 is represented by the dotted line in FIG. 9. The output signal of the pulse discriminator 23 is a pulse signal which is obtained by reversing the $\overline{\text{BORROW}}$ pulse of the 4-bit up-down counter 105 (shown as the signal U in FIG. 9) using the invertor 103.

The time analyzer 24 counts the 24 MHz clock pulses from the generation of the trigger pulse till the reception and generates the count number as its output. The count number corresponds to the propagation time of the ultrasonic wave from the transducer 1 to the crack 7.

Figure 18:
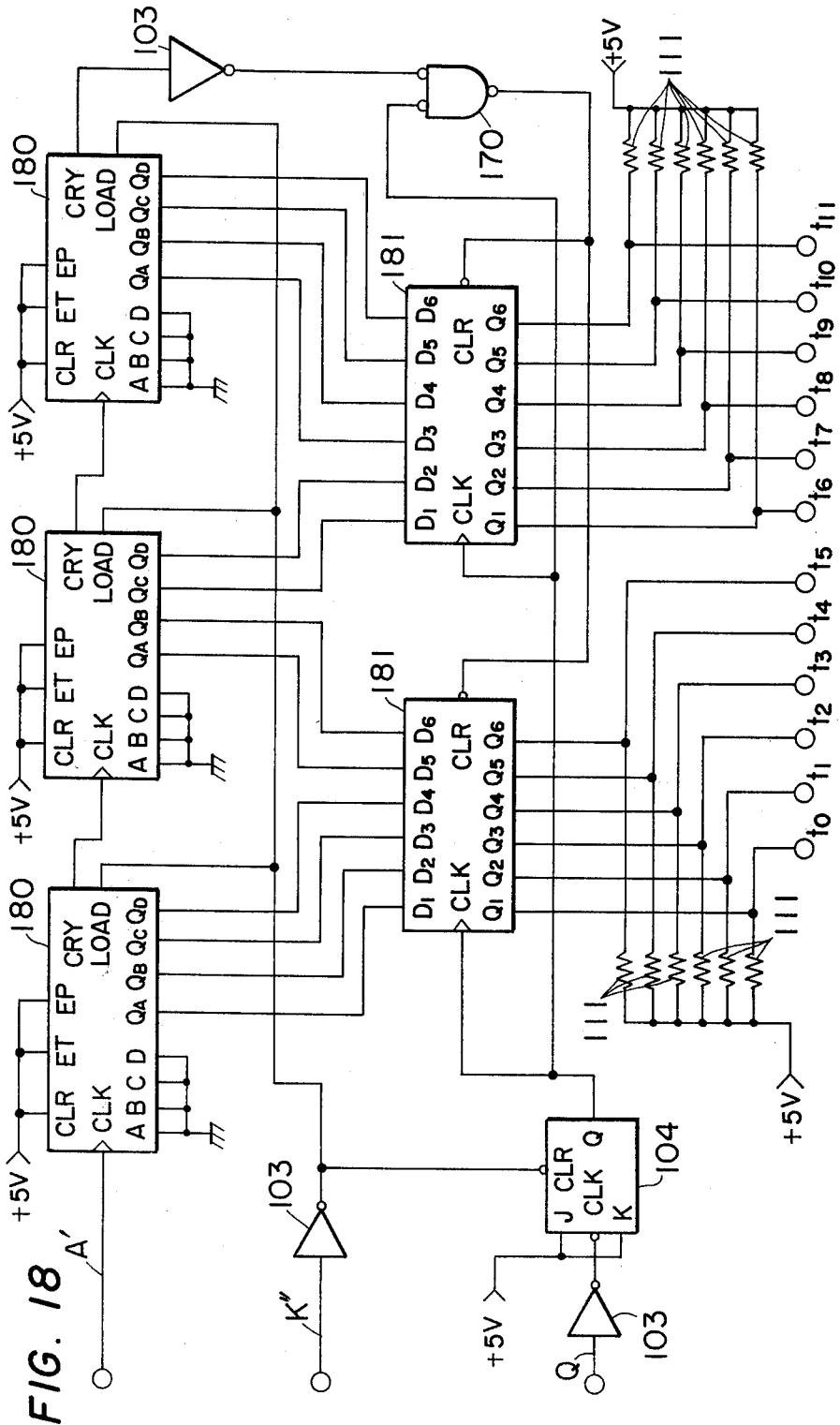
FIG. 18 shows an example of circuit of the time analyzer 24 of FIG. 17.

FIG. 18 shows an example of the circuit construction of the time analyzer 24, wherein an element 180 is a synchronous 4-bit counter which counts the 24 MHz clock pulse (signal A') after generation of the trigger pulse (signal K").

An element 181 is a hexa-D type flip-flop which reads the count number of the synchronous 4-bit counter 180 at the input time of the received pulse (signal Q), holds the value till the subsequent input of the received pulse and produces the value as its output. However, when no received pulse is given as input (where no reflected wave is obtained from the crack 7), all the levels of output signals $t_0$-$t_{11}$ are made "0" when the count number reaches 4096.

The time signals $t_0$-$t_{11}$ is an output signal of the time analyzer 24 and is the count number expressed in the binary notation.

Figure 19:
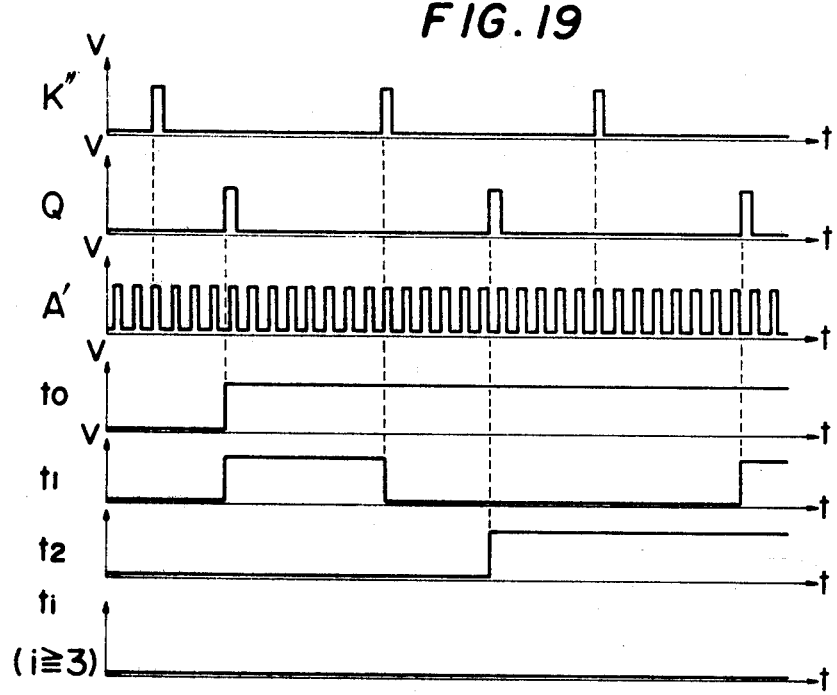
FIG. 19 shows a time chart of the signals in the circuit of FIG. 18.

FIG. 19 shows the time chart of these signals. For example, if there are five 24 MHz clock pulses (signal A') from the input of the trigger pulse (signal K") to the rise of the received pulse (signal Q), the output levels of the signals $t_0$, $t_1$ and $t_2$ are "1", "0" and "1", respectively, and each level is held till the subsequent input of the received pulse.

The counter 25 of FIG. 17 generates as its output a count signal obtained by counting the number of the X-drive pulses and expressing the value in the binary notation after generation of either the reset pulse from the scan controller 10 or the Y-drive pulse, and also a scan direction signal which has a level "1" when the transducer 1 scans on the X-axis in the forward direction on the scanning route 2 and has a level "0" when the transducer 1 scans in the reverse direction.

Figure 20:
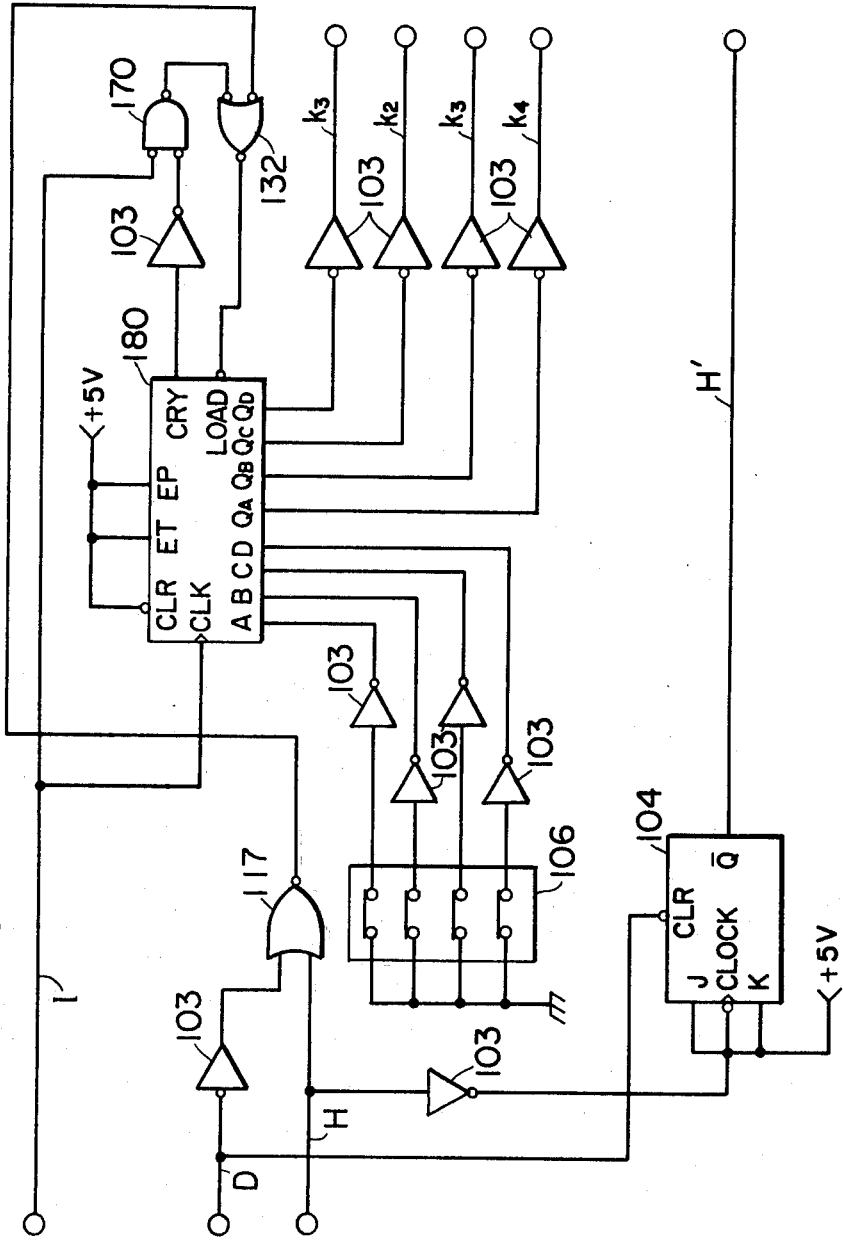
FIG. 20 shows an example of circuit of the counter 25 of FIG. 17.

FIG. 20 shows an example of the circuit construction of the counter 25, wherein an element 180 is a synchronous 4-bit counter, an element 104 is a J-K flip-flop, an element 103 is an invertor, an element 117 is a NAND gate, an element 11 is a resistor and an element 106 is a switch.

The input signals I, D, H of the counter 25 are respectively the X-drive pulse, reset pulse and Y-drive pulse from the scan controller 10. The outputs of the counter 25 are signals $k_0$, $k_1$, $k_2$, $k_3$ and H'.

Figure 21:
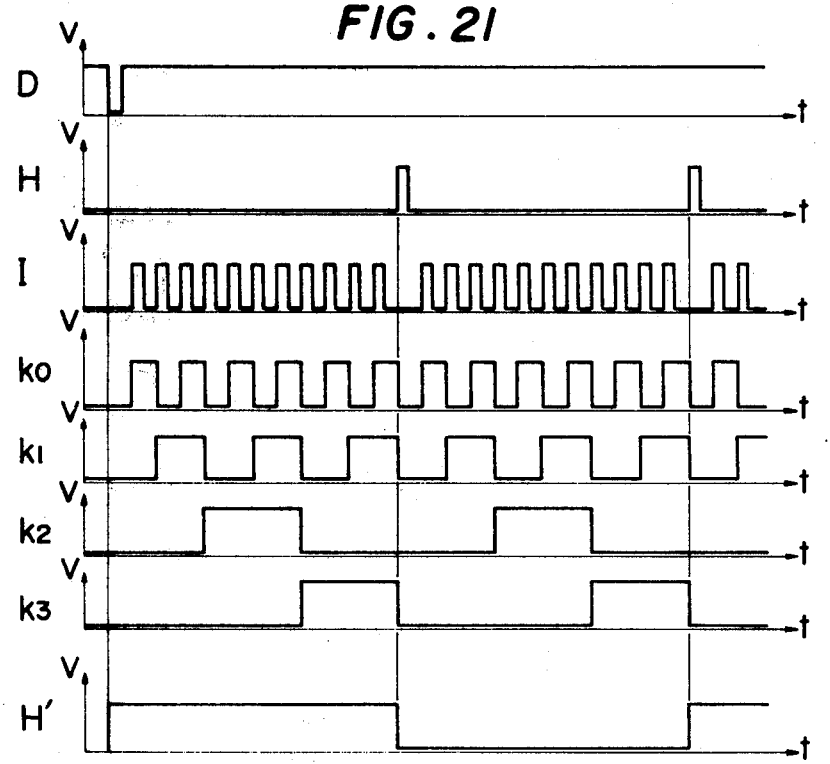
FIG. 21 shows a time chart of the signals in the circuit of FIG. 20.

FIG. 21 shows the time chart of these signals. The output levels of the signals $k_0$, $k_1$, $k_2$, $k_3$ express in terms 8 the 4-bit binary the pulse number of the X-drive pulse (signal I) after generation of the reset pulse (signal D) or the Y-drive pulse (signal H). Accordingly, the output levels of the signals $k_0$, $k_1$, $k_2$, $k_3$ become the same pattern as one another every time when the pulse number of the X-drive pulse increases by 16.

The output level of the signal H' becomes "1" after generation of the reset pulse output and thereafter the level changes every time the Y-drive pulse is generated as output.

The interface 26 of FIG. 17 functions to produce as its output the signal input to the arithmetic unit 27 and the result of operation of the unit 27. The function of the interface 26 is as follows.

For example, the interface produces a 16-notational number $K_x$ in response to the output level of the count signals $k_0$, $k_1$, $k_2$, $k_3$ from the counter 25. It also produces a numeric value $n_d$ in response to the level "1" or "0" of the output level of the scan direction signal, and a 16-notational number $N_t$ in response to the output levels of the time signals $t_0$–$t_{11}$ from the time analyzer 24. It sets a 16-notational number $n_c$ corresponding to the frequency-division value n of the clock pulse in Examples 1 and 2 and a numeric value $N_p$ for causing the arithmetic unit 27 to perform the operation. For completing the operation, $N_p$ is made O. It sets a numeric value $N_R$ in order to transfer numeric values $n_c$, $n_d$, $K_x$, $N_t$ from the interface 26 to the arithmetic unit 27. The value NR is 1 during the period from the generation time of the trigger pulse till the transfer time and is 0 at other times. The operation result of the arithmetic unit 27 is produced as its output either as 0 or 1 and in response to this operation result, the interface 26 outputs the luminance signal having the output level of "0" or "1" to the display. However, the output level of the luminance signal is held till the subsequent operation result is generated as output from the arithmetic unit 27.

The above is an example of the action of the interface 26.

Figure 22:
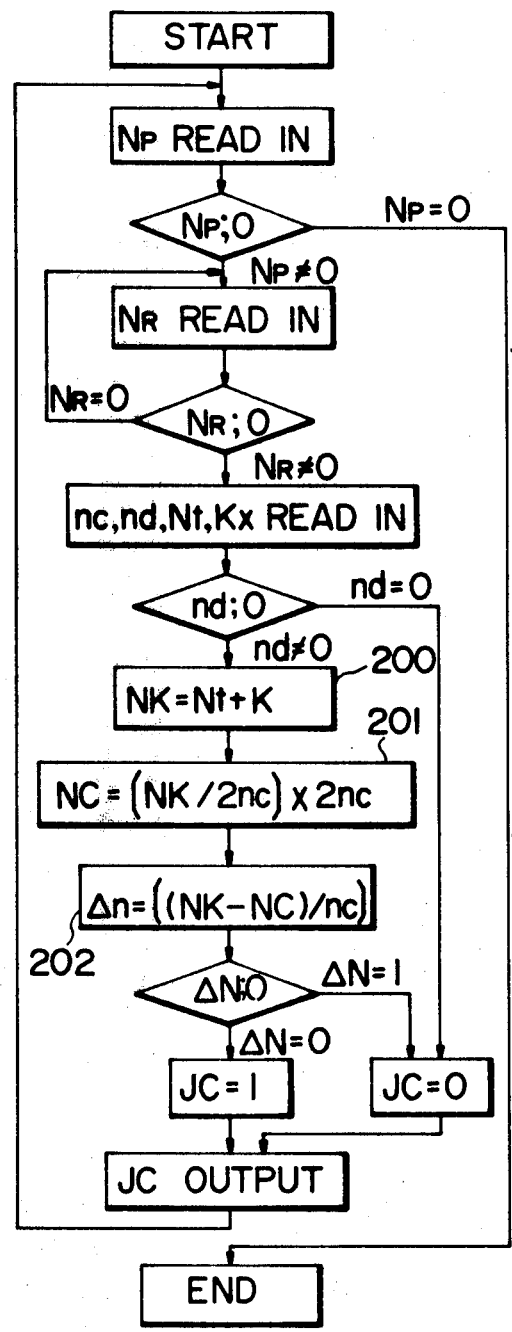
FIG. 22 shows an example of flow chart of the operation content of the arithmetic unit 27 of FIG. 17.

Next, the explanation will be given on the operation content of the arithmetic unit 27 with reference to the flow chart. FIG. 22 shows the flow chart of the operation content.

The arithmetic unit 27 firsts reads in $N_p$ and after confirming that $N_p=0$, it makes the subsequent operation.

The unit reads in $N_R$ and then $n_c$, $n_d$, $N_t$ and $K_x$ when $N_R=1$. When $N_R=0$, it awaits until $N_R$ becomes 1, that is to say, until the trigger pulse is applied as input to the interface 26. After reading $n_c$, $n_d$, $N_t$ and $K_x$, it discriminates whether $n_d$ is 0 or 1. When $n_d=0$, it corresponds to the state where the transducer 1 is caused to scan on the X-axis of the scanning route 2 in the reverse direction. Hence, JC is set to 0 and its value is output to the interface 26. Next, when $n_d=1$, it performs the operation expressed by the operation formulas 200, 201 and 202. The symbol in the square bracket [ ] in the operation formulas 201 and 202 expresses the Gaussian symbol and represents the maximum integer not exceeding the numeric value in the square bracket [ ].

From the value ΔN obtained by the numeric operation, the value JC is applied as output to the interface 26 with JC=0 when ΔN=0 and JC=1 when ΔN=1. After the output is completed, the unit again starts reading $N_p$ and thereafter repeats the abovementioned operational processing.

The luminance signal generated as output from the interface 26 on the basis of the output value JC from the arithetic unit 27 corresponds to the coincidence signal of Example 1 shown in FIG. 2. The luminance signal obtained when NK=(N−K) in the operation formula 200 of FIG. 22 corresponds to the coincidence signal of Example 2 shown in FIG. 12.

When NK=Nt in the operation formula 200 of FIG. 22, the state corresponds to the case where the trigger pulse is synchronized with the frequency-division clock pulse in Examples 1 and 2.

Using the luminance signal output from the interface 26, the display 12 displays the hologram of the crack 7.

Next, the explanation will be given about the hologram of the object obtained by the conventional holography crack-detection apparatus and the definite example of the hologram of the object obtained by the apparatus illustrated in Example 1 of the present invention.

Figure 23:
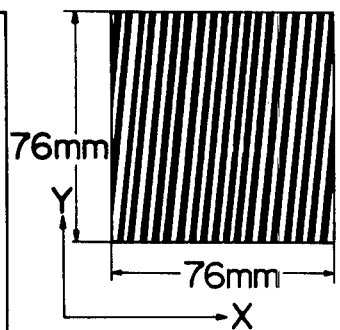
FIG. 23 shows the hologram obtained by the conventional ultrasonic holography apparatus.

The conventional ultrasonic holography apparatus uses a transducer having a resonance frequency 3 MHz and a ultrasonic pulse of a sine wave mode having a frequency of 3 MHz and a pulse width of 15 μS. The resulting hologram is illustrated in FIG. 23. In the drawing, x- and y-directions respectively correspond to the scanning directions of the transducer. The gap of the interference fringes displayed as the hologram is 4.0±0.2 mm.

On the other hand, the apparatus (Example 1) of the present invention uses a transducer of a resonance frequency of 1 MHz and a ultrasonic wave having a frequency of 1 MHz and a pulse width of 2 μS whereby the frequency of the frequency-division clock pulse is 3 MHz.

Figure 24:
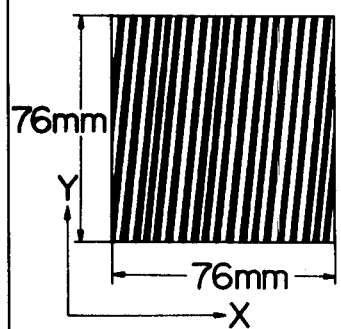
FIG. 24 shows the hologram obtained by the apparatus of the present invention shown in Example 1.

The resulting hologram is illustrated in FIG. 24. In the drawing, x- and y-axes are the same as those in FIG. 23. In FIG. 24, the gap of interference fringes is 3.9±0.2 mm and this is in conformity with the gap of interference fringes of the hologram obtained by the conventional apparatus, i.e., 4.0±0.2 mm, within an allowable error range.

The following can be confirmed from the abovementioned results.

1. The conventional ultrasonic holography apparatus forms hologram by the use of a ultrasonic pulse of a sine wave mode. In accordance with the apparatus of Examples 1 through 3 of the present invention, it is now possible to prepare the hologram even by the use of a spike-shape ultrasonic pulse.

2. In the apparatus of Examples 1 through 3 of the invention, the frequency of the clock pulse corresponds to the ultrasonic frequency used in the conventional apparatus.

Accordingly, if the frequency of the clock pulse is 3 MHz in the apparatus in Examples 1 through 3 of the present invention, it is possible to obtain the hologram having the same gap of interference fringes as that of the hologram obtained by the conventional apparatus which uses the transducer having the 3 MHz resonance frequency and the 3 MHz ultrasonic wave. It is possible, for example, by the use of a 6 MHz clock pulse even when an 1 MHz ultrasonic wave is used in the present apparatus, to obtain the hologram which is the same as the one obtained by the conventional apparatus using the 6 MHz ultrasonic wave.

Where it is desired to observe three-dimensionally the condition of the crack not only to evaluate the position, shape and size of the crack from the resulting hologram, it is necessary to reproduce the image. However, the hologram prepared by the above-described apparatus contains only the phase difference information but no amplitude information. Accordingly, when the image is reproduced, high dimensional interference fringes appear on the reproduced image whereby the image tends to become unclear. This problem can be solved by varying the luminance level of the coincidence signal obtained in the aforementioned Examples 1 through 3 in proportion to the intensity of the reflected wave signal from the object for crack-detection.

An example of the apparatus capable of producing a hologram which contains both phase difference information and amplitude information will be explained in the following paragraph.

Figure 25:
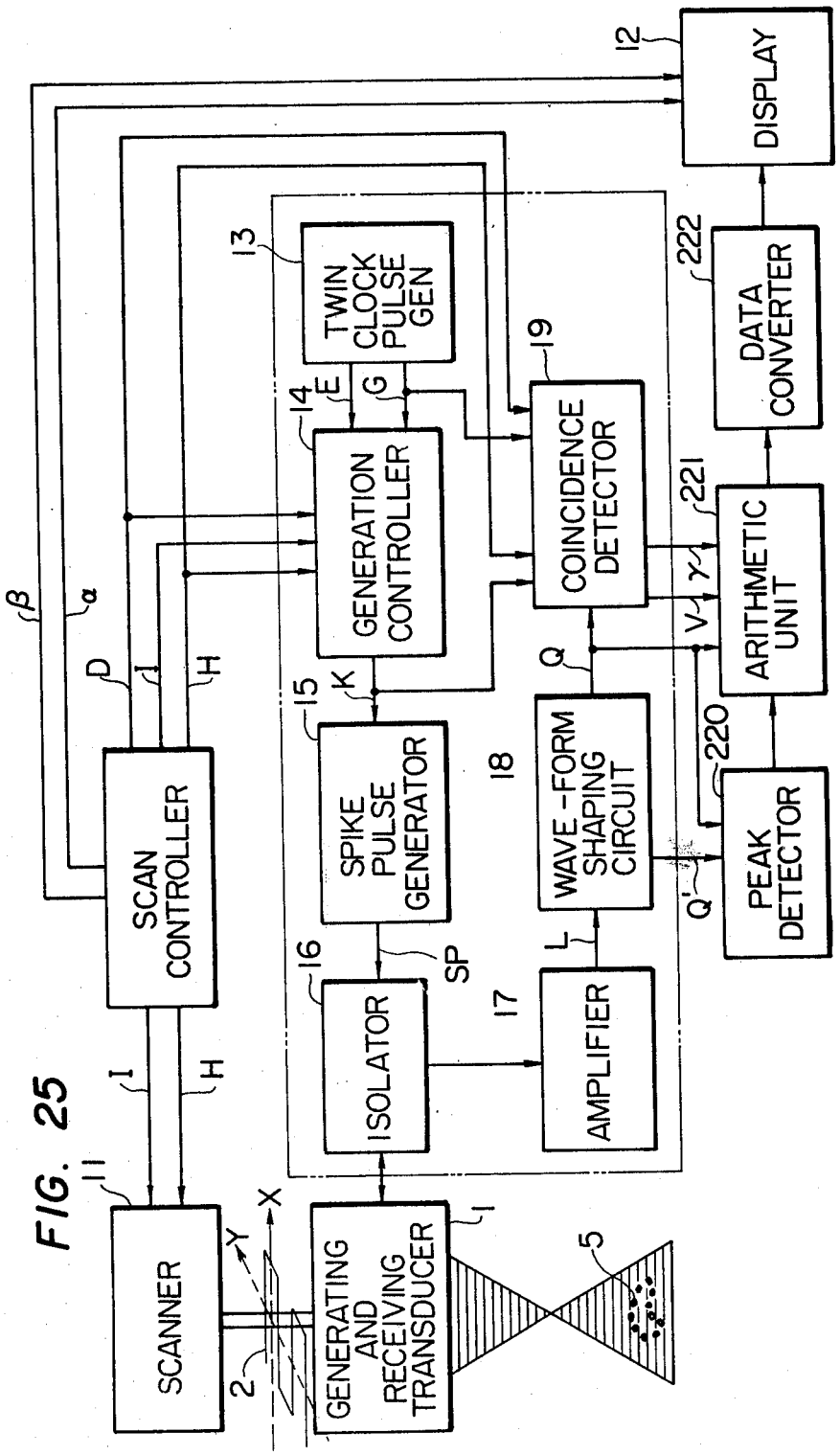
FIG. 25 shows the construction of the apparatus of Example 4 of the present invention.

FIG. 25 shows the overall construction of the fourth Example of the present apparatus which is able to produce the hologram capable of providing a clear reproduction image.

In FIG. 25, instruments other than those encompassed by thick frames have the same function as those shown in FIG. 2. The portions encircled by the dotted lines especially have the same function as the digital type ultrasonic holography crack-detection apparatus shown in FIG. 2. In order to assist the easy understanding, a brief explanation will be given about the instruments other than those encircled by the thick frames.

Figure 26:
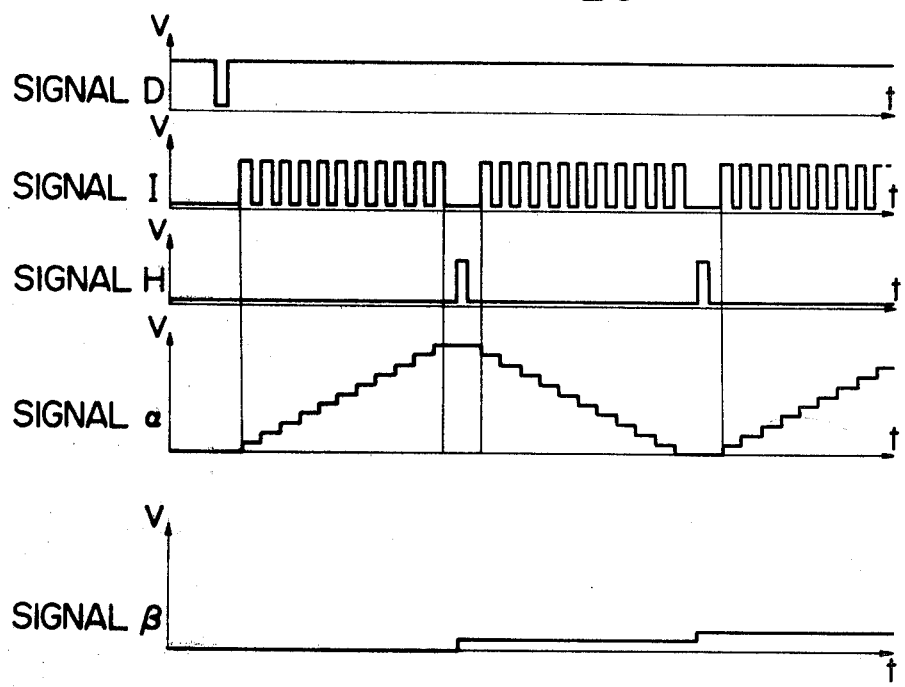
FIG. 26 shows a time chart of the output signals of the scan controller 10 of FIG. 25.

The scanner 11 causes the transducer 1 to scan along the scanning route 6 on the X-Y plane. The scan controller 10 produces as its output a control signal for driving the scanner 11. The output signals are those represented by D, I, H, $\alpha$ and $\beta$ in FIG. 26 that are respectively the reset pulse, X-drive pulse, Y-drive pulse, and X- and Y-coordinate signals. The transducer 1 is driven in the X direction at the time of output of the X-drive pulse I and in the Y-direction at the time of output of the Y-drive pulse H whereby the transducer is actuated along the scanning route represented by 6 in FIG. 26. The reset pulse D is a pulse which is generated as output at the start of scanning. X- and Y-coordinate signals are those which respectively indicate the position of the transducer 1 on the X-Y plane and they are generated, for example, as the analog quantity obtained by digital-analog conversion of the number of X- or Y-drive pulse after the output of the reset pulse.

Figure 27A:
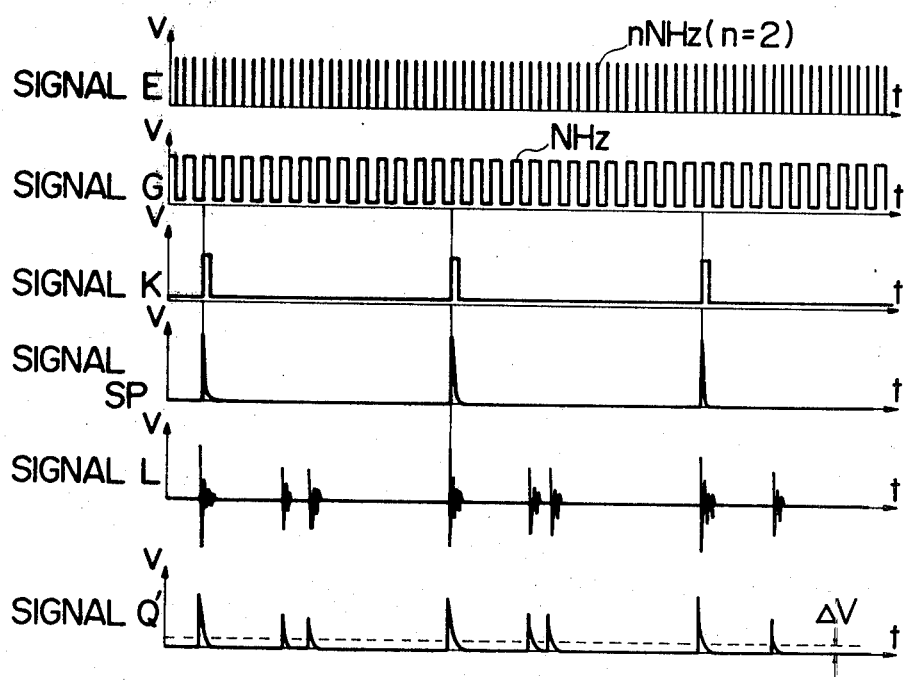
FIGS. 27a and 27b shows a time chart of input and output signals to and from means encircled by dotted lines in FIG. 25.
Figure 27B:
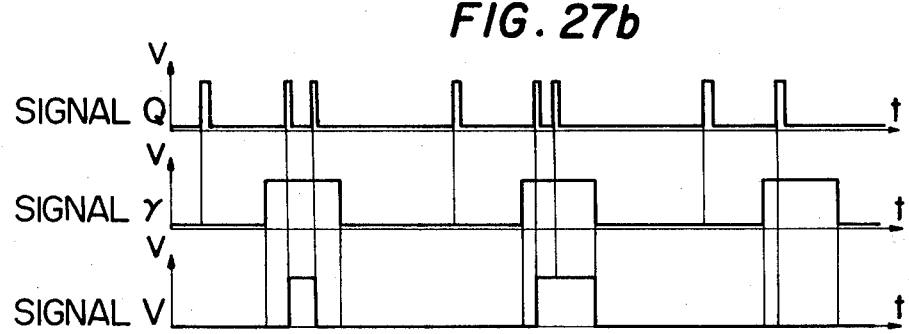

Referring to FIGS. 25 and 27, the twin clock pulse generator 13 generates an nN Hz clock pulse E and an N Hz clock pulse G obtained by dividing the frequency of E by n. The generation controller 14 generates as its output a trigger pulse K in synchronism with or retardance from the rise of the N Hz clock pulse G. The delay time in the case of retardance is set so as to correspond to the number of nN Hz clock pulses in proportion to the number of the X-drive pulse I after generation of the reset pulse D or the Y drive pulse H. The spike pulse generator 15 outputs a spike pulse SP of a high voltage in synchronism with the trigger pulse K. The isolator 16 supplies the spike pulse SP to the transducer 1 and on the contrary, supplies the object modified wave produced as output from the transducer 1 to the amplifier 17. The amplifier 17 amplifies the object modified wave and supplies as its output the resulting amplificaton signal L to the waveform shaping circuit 18. The waveform chart of the signal L in FIG. 27 indicates the amplification signals of the received pulses observed in synchronism with the spike pulse SP and those of the object modified wave from the reflection object 5 thereafter observed.

The waveform shaping circuit 18 detects the amplification signal L to obtain the detection signal Q' and further converts the detection signal Q' into a digital pulse of which portion exceeding the threshold level V has a TTL level "1". The coincidence detector 19 produces a gate pulse $\gamma$ of a predetermined width from the received pulse among those received pulses Q which are fed from the waveform shaping circuit 18 after the passage of a predetermined period from the generation of the trigger pulse, and extracts only the received pulse obtained in the time set by the gate pulse among the received pulses Q from the waveform shaping circuit 18, that is to say, the reflected wave from the reflection object 5. The detector subsequently reads the output level of the N Hz clock pulse G at the rise of the extracted pulse and produces the level as its output. This output level is read by the subsequent received pulse and held till the read value becomes the 0 level or the gate pulse falls. The signal is output as a coincidence pulse V.

Next, the action of the instruments indicated by the thick frames in FIG. 25 wil be explained.

Figure 28:
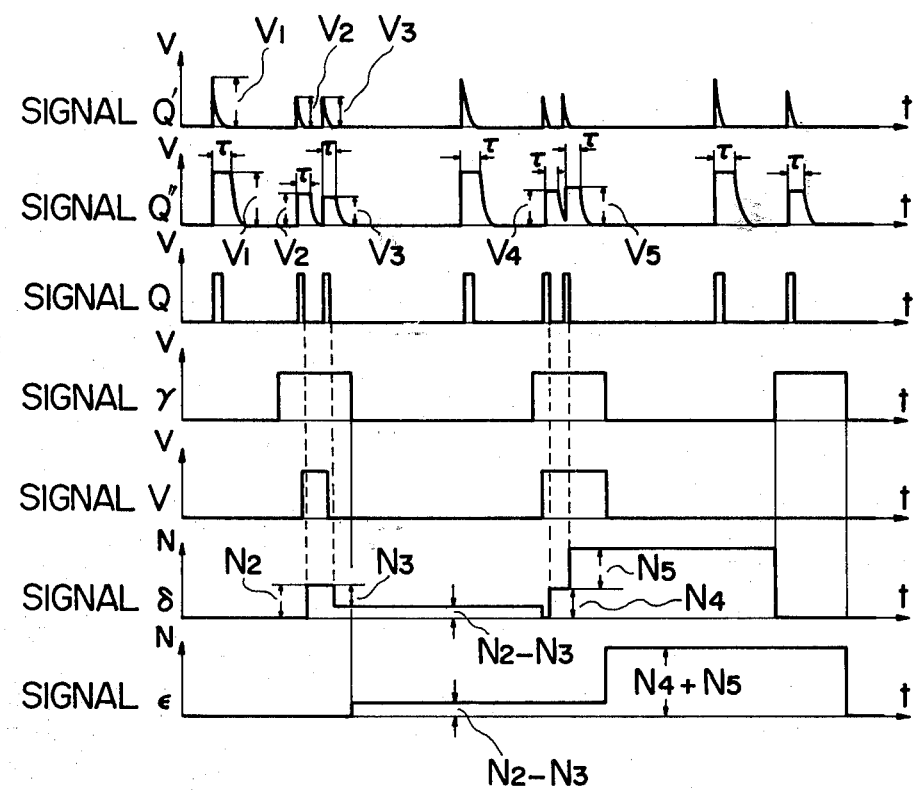
FIG. 28 shows a time chart of input and output signals to and from each means encircled by thick frames in FIG. 25.
Figure 29:
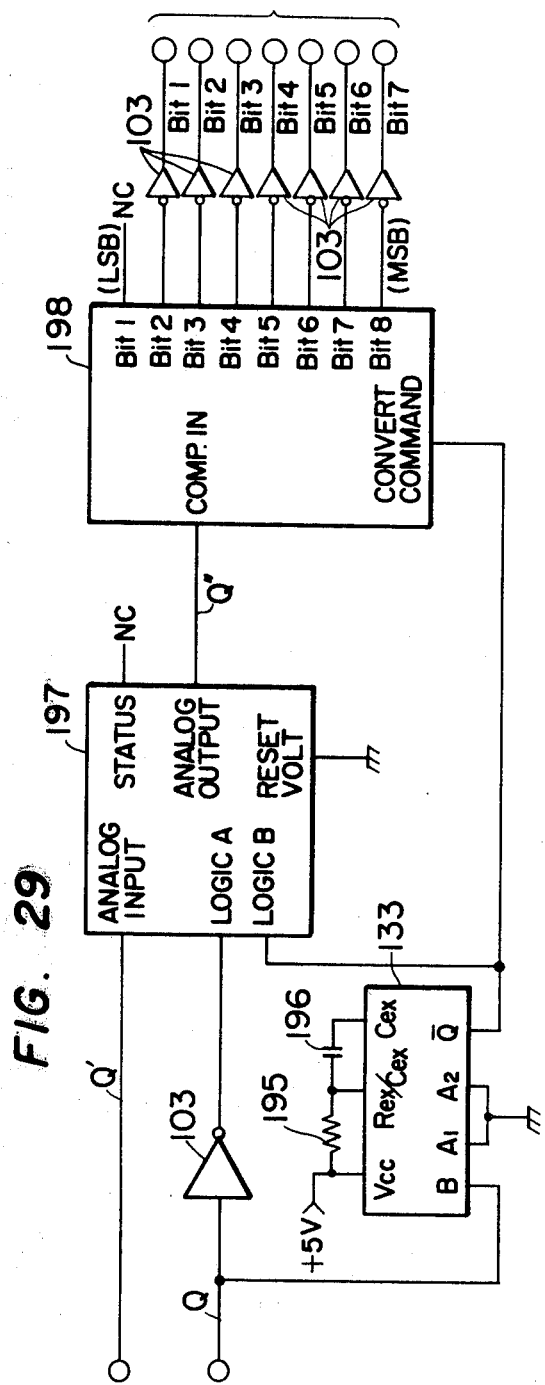
FIG. 29 shows in detail the construction of the peak detector 220 of FIG. 25.

FIG. 29 shows a detailed circuit diagram of the peak detector 220. The detection signal (Q in FIGS. 27 & 28) obtained by the waveform shaping circuit 17 is converted into a peak detection signal indicated by Q" in FIG. 28 and its value is converted into a digital quantity of binary seven bits. The peak detection of this circuit is carried out by producing a negative logical pulse having a width longer than the pulse width of the received pulse (Q in FIG. 28) from the waveform shaping circuit 18 by the use of a mono-stable multi-vibrator 133 and holding the maximum value of the detection signal to a constant level in proportion to the pulse width of this signal over a time period. The period for holding the maximum value to a constant level is determined by the difference between the time constants of the resistor element 195 and the capacitor 196 wired to the mono-stable multi-vibrator 133 and the pulse width of the received pulse Q.

A peak detection element 197 is used for converting the detection signal Q' to the peak detection signal Q" and an analog-digital converter 198 is used for converting the voltage value of the peak detection signal Q" into a digital quantity of binary seven bits. Incidentally, an IC element 103 in FIG. 29 represents an invertor element.

Figure 30:
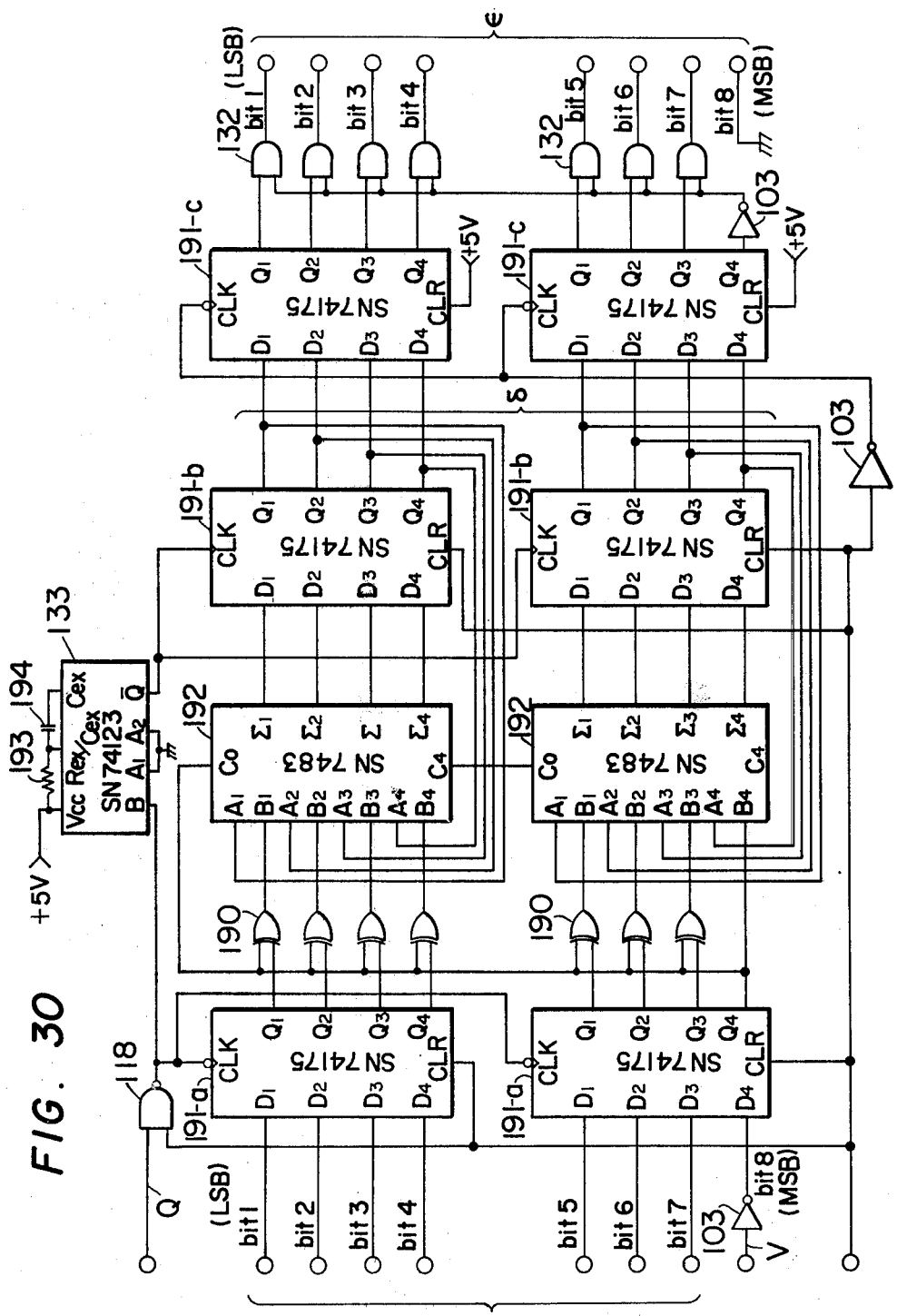
FIG. 30 shows in detail the construction of the arithmetic unit 221 of FIG. 25.

FIG. 30 shows a detailed circuit diagram of the arithmetic unit 221. A registor 191-$a$ is set to 0 at the time of rise of the gate pulse ($\gamma$ in FIGS. 27 & 28), and thereafter a peak value (digital quantity of binary seven bits)

from the peak detector 220 is read at the fall of the received pulse (Q in FIG. 28) which is received during generation of the gate pulse. The peak value is read in such a manner as to make adding when the output level of the coincidence pulse (V in FIGS. 27 & 28) at this time is "1" and substraction when the output level is "0" and is subjected to either adding or subtraction by an adder-subtracter IC element 192. The operated value of each operation is once latched by a resiter 191-b and the latched value is again loaded by the adder-subtracter IC element, thereafter sequentially repeating the adding or subtraction of the peak value at the fall of the subsequent received pulse.

The content of the register 191-b is latched by a register 191-c at the time of fall of the gate pulse γ and the content of the register 191-c is digitally output as an operation value. However, when the operation value is negative, the output is 0. FIG. 28 shows an example of the latch content of the register 191-b. In δ of FIG. 28, integer values $N_2$, $N_3$, $N_4$, $N_5$ indicate digital values obtained by the A-D conversion of peak voltages $V_2$, $V_3$, $V_4$, $V_5$ at the peak detector 220 indicated respectively at Q". The operation output of the arithmetic unit 221 is shown at ε in FIG. 28. The operation value output at the fall of the gate pulse is held till the fall of the subsequent gate pulse. An IC element 133 shown in FIG. 30 represents a mono-stable multi-vibrator, which is determined by the time constant of a resistor element 193 and that of the capacitor 194. This pulse causes the register 191-b to make latching action belatedly with respect to the fall time of the received pulse Q. An IC element 103 is an invertor, an IC element 118 is a NAND gate, an IC element 132 is an AND gate and an IC element 190 is a gate.

The data converter 220 converts the operation value from the unit 221 from the digital value into the analog value and applies it as output to the display 12. The display displays the hologram by the use of the X- and Y-coordinate signals from the scan controller 10 as the deflection signal and the signal from the data convertor as the luminance signal.

The above is an example of the action of the apparatus of Example 4 of the present invention.

Additionally, it is possible to display the hologram of a 0-1 pattern on the display 12 by using a digital comparator as means for the D-A conversion function instead of the data convertor 220 of FIG. 25 and producing as output the signals of a "0" level and "1" level respectively when the operation value of the arithmetic unit 221 is O and a positive value. This case is the same as the apparatus shown in FIGS. 1 through 3 in that they all provide the hologram of the 0-1 pattern. However, whereas the apparatus in Examples 1 through 3 discriminates the time coincidence between one reflected wave and the clock pulse, the apparatus of Example 4 discriminates synthetically and numerically the time coincidence between all of plural reflected waves and the clock pulse with a high level of accuracy so that it is possible to prepare a hologram consisting of individual holograms of the plural reflection bodies superposed and put together.

As explained in the foregoing paragraph, there are provided the following effects in accordance with the present invention;

1. It is possible to control the gaps of interference fringes irrespective of the ultrasonic frequency used. For example, it is possible to produce a detailed hologram having narrow gaps of interference fringes by increasing the frequency of the frequency-division clock pulse in the apparatuses of Examples 1 and 2 and by setting the value no to a small value in the apparatus of Example 3.

2. It is possible to use a pulse of a spike-shape as the generation pulse. Accordingly, the reflected waves from plural adjacent bodies can be easily discriminated rime-wise and hence, time resolution capacity is improved in comparison with the conventional ultrasonic holography apparatus using a pulse of a sine wave mode.

3. It is possible to produce a hologram capable of reproducing an image of less bleeding in the same way as a ultrasonic halography apparatus which causes the transmissive wave or the reflected wave to interfere with the reference wave.

4. It is possible to produce a hologram consisting of plural holograms superposed with one another when a plurality of reflection bodies are present.

What is claimed is:

1. A digital type ultrasonic halography apparatus comprising:
   first means for generating a first clock pulse which changes periodically in its level between a high state and a low state,
   second means for transmitting an ultrasonic pulse toward an object in synchronism with the first clock pulse, and receiving an ultrasonic pulse reflected by the object, the repetition interval of the transmitted pulse being larger than the period of the first clock pulse, and
   third means for detecting the state of the first clock pulse when the intensity of the received ultrasonic pulse reaches a predetermined level, to generate a coincidence signal only when the detected state is a predetermined one, to produce a hologram of the object with the coincidence signal.

2. The digital type ultrasonic holography apparatus as defined in claim 1, which further includes fourth means for scanning the object with an ultrasonic generating and receiving transducer included in the second means by moving the transducer over the object in a coordinate X-Y plane, and generating a position signal which represents the position of the transducer.

3. The digital type ultrasonic holography apparatus as defined in claim 2, further including means for displaying the hologram of said object, the coincidence signal of the third means being used as a luminance signal for the display means and the position signal of the fourth means being used as a deflection signal for the display means.

4. The digital type ultrasonic holography apparatus as defined in claim 2, which further includes means for generating a second clock pulse, and means connected to the second means for generating a trigger pulse in synchronism with the rise or the fall of the second clock pulse, the repetition interval of the trigger pulse being larger than the period of the second clock pulse, wherein said transducer transmits the ultrasonic pulse in synchronism with the rise or the fall of the trigger pulse.

5. The digital type ultrasonic holography apparatus as defined in claim 4, which further includes means connected to the second means for delaying said trigger pulse, the delay time being changed according to the position of said transducer.

6. The digital type ultrasonic holography apparatus as defined in claim 2, wherein the third means comprises means for measuring a time duration $t_p$ between the transmitted ultrasonic pulse and the received ultrasonic pulse, and means for dividing the time duration by the value $T_c$ which equals the period of the first clock pulse and generating said coincidence pulse when the remainder $\delta$ of the division is in the range $0 \leq \delta < T_c/2$.

7. The digital type ultrasonic holography apparatus as defined in claim 1, which further includes means for detecting a peak value of the received ultrasonic pulse, means for adding or reducing the peak values of each of the received ultrasonic pulses obtained by one ultrasonic pulse transmission, according to the state of said coincidence signal, and means for holding the output signal of the adding or reducing means at the end of the predetermined period, to produce the hologram of said object with the output signal of the holding means.

8. The digital type ultrasonic holography apparatus as defined in claim 7, which further includes fourth means for scanning the object with an ultrasonic generating and receiving transducer included in the second means by moving the transducer over the object in a coordinate X-Y plane, and generating position signals which represent the position of the transducer.

9. The digital type ultrasonic holography apparatus as defined in claim 8, which includes means for converting the output signal of the holding meansinto an analog signal, and means for displaying the hologram of said object, the output signal of said converting means being used as a luminance signal for the displaying means and the position signal of the fourth means being used as a deflection signal for the displaying means.

10. A digital type ultrasonic holography apparatus comprising:

first means for generating a first clock pulse which changes periodically in its level between a high state and a low state, having a frequency of nN MHz, where n and N are both integers;

second means for generating a second clock pulse which changes periodically in its level between a high state and a low state by frequency dividing said first clock pulse by n so that said second clock pulse has a frequency of N MHz;

third means for transmitting an ultrasonic pulse toward an object in accordance with the rise time of the second N MHz clock pulse delayed by an integer m times the period of the first nN MHz clock pulse;

means for receiving an ultrasonic pulse reflected from the object;

means for comparing the received pulse with a predetermined voltage and providing an output detection signal Q when the received pulse exceeds the predetermined voltage; and coincidence detecting means coupled to the output of the comparing means for producing a coincidence signal to produce a hologram of the object by detecting the state of the second N MHz clock pulse when the detection signal Q is received by the coincidence detection means, wherein said coincidence signal is only generated when the detected state is a predetermined one.

11. A digital type ultrasonic holography apparatus according to claim 10, further including means for scanning the object with an ultrasonic generating and receiving transducer forming part of said transmitting and receiving means, and means for generating a position signal in accordance with the position of the transducer, wherein the integer m is determined in accordance with the position signal.

12. A digital type ultrasonic holography apparatus comprising:

means for transmitting an ultrasonic pulse toward an object in accordance with a trigger pulse generated by a trigger pulse generator;

means for receiving a reflected ultrasonic wave from the object;

means for generating a clock pulse which changes periodically in its level between a high state and a low state which clock pulse is delayed from the trigger pulse by a time determined by the position of an ultrasonic generating and receiving transducer which is part of the transmitting and receiving means; and means for detecting the state of the clock pulse when the intensity of the received ultrasonic pulse reaches a predetermined level, to generate a coincidence signal only when the detected state is a predetermined one, to produce a hologram of the object with the coincidence signal.

* * * * *